US012655082B2

(12) United States Patent
Roettger et al.

(10) Patent No.: US 12,655,082 B2
(45) Date of Patent: Jun. 16, 2026

(54) PROCESS FOR THE ENERGY-EFFICIENT PREPARATION OF ALKALI METAL ALCOHOLATES

(71) Applicant: EVONIK OPERATIONS GMBH, Essen (DE)

(72) Inventors: Dirk Roettger, Cologne (DE); Sebastian Reimann, Wesseling (DE); Niklas Paul, Marl (DE); Armin Matthias Rix, Marl (DE); Philip Zitzewitz, Haltern am See (DE); Moritz Schröder, Münster (DE)

(73) Assignee: Evonik Operations GmbH, Essen (DE)

( * ) Notice: Subject to any disclaimer, the term of this patent is extended or adjusted under 35 U.S.C. 154(b) by 500 days.

(21) Appl. No.: 18/275,469

(22) PCT Filed: Jan. 27, 2022

(86) PCT No.: PCT/EP2022/051869
§ 371 (c)(1),
(2) Date: Aug. 2, 2023

(87) PCT Pub. No.: WO2022/167311
PCT Pub. Date: Aug. 11, 2022

(65) Prior Publication Data
US 2024/0308942 A1 Sep. 19, 2024

(30) Foreign Application Priority Data
Feb. 5, 2021 (EP) ...................................... 21155473

(51) Int. Cl.
*C07C 29/70* (2006.01)
*C07C 29/80* (2006.01)

(52) U.S. Cl.
CPC .............. *C07C 29/70* (2013.01); *C07C 29/80* (2013.01)

(58) Field of Classification Search
CPC ......... C07C 29/70; C07C 29/80; C07C 31/30; Y02P 20/10
See application file for complete search history.

(56) References Cited

U.S. PATENT DOCUMENTS 1,910,331 A 5/1933 Halbig
2,295,256 A 9/1942 Brugma
(Continued)

FOREIGN PATENT DOCUMENTS

CA 1242309 9/1988
CN 105218315 1/2016
(Continued)

OTHER PUBLICATIONS

English language translation of the International Search Report for international application PCT/EP2022/057591 filed Mar. 23, 2022, corresponding to copending U.S. Appl. No. 18/570,519.
(Continued)

*Primary Examiner* — Jafar F Parsa
(74) *Attorney, Agent, or Firm* — Law Office of: Michael A. Sanzo, LLC

(57) ABSTRACT

The present invention relates to a process for preparing alkali metal alcoholates in counter flow by way of reactive rectification, the alkali metal being selected from sodium and potassium. The process is carried out in at least one reaction column and at least one rectification column. The process according to the invention is characterized in that the heating steam used for operating the columns and thus for carrying out the process condenses, and that the energy is used in the condensed water.

20 Claims, 5 Drawing Sheets

(56)                References Cited

U.S. PATENT DOCUMENTS

Figure 1:
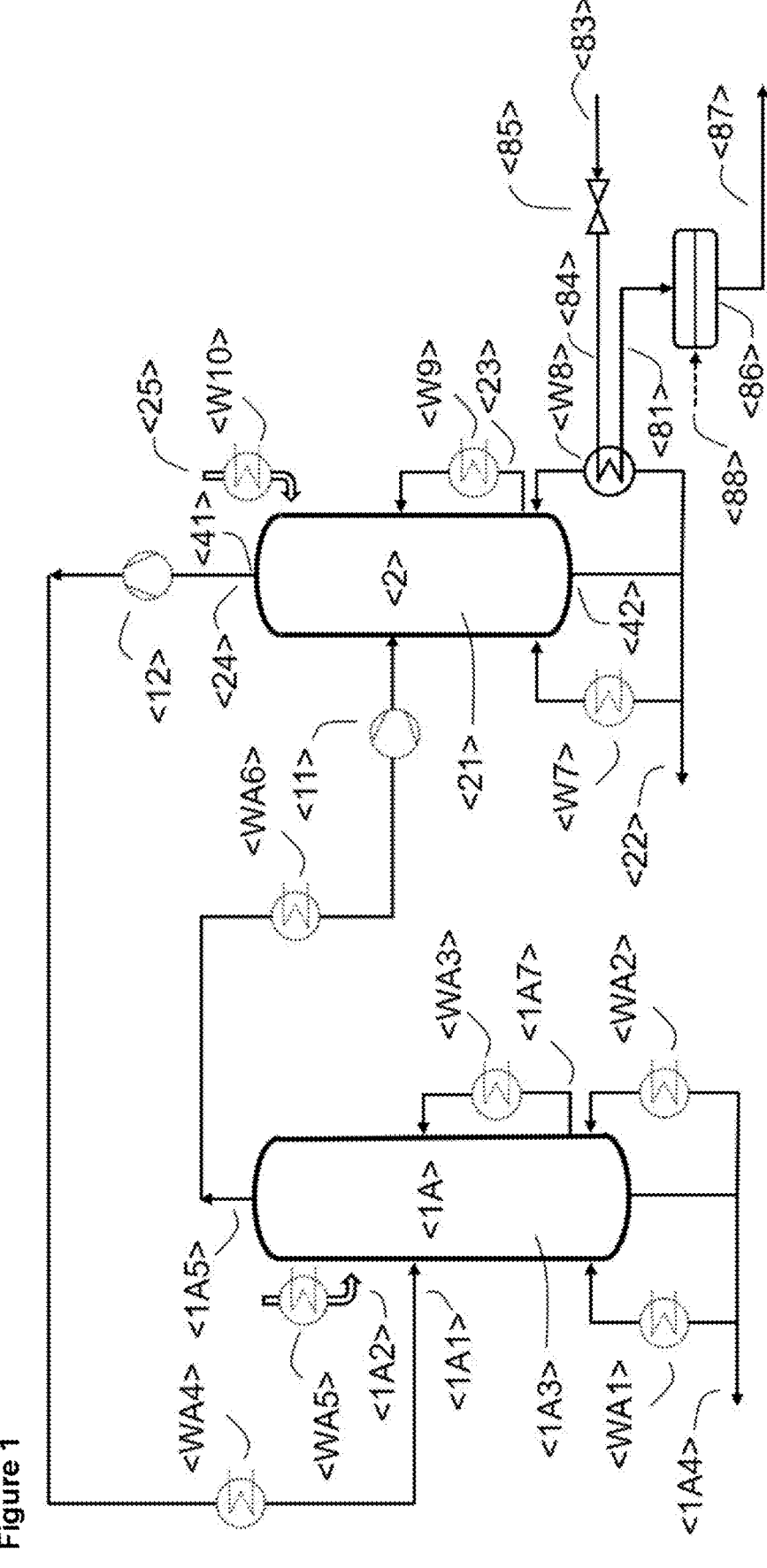

| 2,877,274 | A | 3/1959 | Kramis |
| 3,418,383 | A | 12/1968 | Lenz et al. |
| 4,327,230 | A | 4/1982 | Ackermann et al. |
| 4,566,947 | A | 1/1986 | Tsuruta |
| 4,895,989 | A | 1/1990 | Sander et al. |
| 6,759,560 | B2 | 7/2004 | Guth et al. |
| 7,847,133 | B2 | 12/2010 | Ruwwe et al. |
| 8,069,687 | B2 | 12/2011 | Jork et al. |
| 11,634,372 | B2 | 4/2023 | Roettger et al. |
| 11,661,388 | B2 | 5/2023 | Roettger et al. |
| 11,746,075 | B2 | 9/2023 | Roettger et al. |
| 2011/0313207 | A1 | 12/2011 | Kaibel et al. |
| 2020/0148706 | A1 | 5/2020 | Sakurai et al. |
| 2022/0340509 | A1* | 10/2022 | Roettger ................. C07C 29/70 |
| 2023/0028559 | A1 | 1/2023 | Roettger et al. |

FOREIGN PATENT DOCUMENTS

| DE | 968903 | 4/1958 |
| EP | 122367 | 10/1984 |
| GB | 377631 | 7/1932 |
| GB | 737453 | 9/1955 |
| WO | WO 2022/263032 | 12/2022 |

OTHER PUBLICATIONS

English language translation of the Written Opinion of the International Searching Authority for international application PCT/EP2022/057591 filed Mar. 23, 2022, corresponding to copending U.S. Appl. No. 18/570,519.

International Preliminary Report on Patentability for international application PCT/EP2022/057591 filed Mar. 23, 2022, corresponding to copending U.S. Appl. No. 18/570,519.

European Search Report and Search Opinion for EP 21179722 filed Jun. 16, 2021, corresponding to PCT/EP2022/057591 filed Mar. 23, 2022, with partial English language machine translation of the Search Opinion.

Dejanovic, et al., "Dividing wall column—A breakthrough towards sustainable distilling," *Chemical Engineering and Processing* 49(6):559-580 (Jun. 2010).

European Search Report and Search Opinion for EP 21155473 filed Feb. 5, 2021, corresponding to PCT/EP2022/051869 filed Jan. 27, 2022, with partial English language machine translation of the Search Opinion.

U.S. Appl. No. 18/570,519, filed Dec. 14, 2023, Roettger.

English language translation of the International Search Report for corresponding PCT/EP2022/051869 filed Jan. 27, 2022.

English language translation of the Written Opinion of the International Searching Authority for corresponding PCT/EP2022/051869 filed Jan. 27, 2022.

International Preliminary Report on Patentability for corresponding PCT/EP2022/051869 filed Jan. 27, 2022.

European Search Report for EP 21155473 filed Feb. 5, 2021.

Translation of Office Action dated Nov. 14, 2022 from corresponding Taiwan examination proceeding.

"Gas/Liquid Separation Technology," (2018); found at http://www.sulzer.com/-/media/files/products/separation-technology/feed-inlet-devices/gas_liquid_technology.ashx?la=en.

U.S. Appl. No. 17/659,086, filed Apr. 13, 2022, US-2022/0340509 A1, Oct. 27, 2022, Roettger.

U.S. Appl. No. 17/759,143, filed Jul. 20, 2022, US-2023/0028559 A1, Jan. 26, 2023, Roettger.

* cited by examiner

PROCESS FOR THE ENERGY-EFFICIENT PREPARATION OF ALKALI METAL ALCOHOLATES

CROSS REFERENCE TO RELATED APPLICATION

The present application is US national stage of international application PCT/EP2022/051869, which had an international filing date of Jan. 27, 2022 and which was published on Aug. 11, 2022. The PCT application claims priority to EP 21155473.8, filed on Feb. 5, 2021. The content of these prior filings is hereby incorporated by reference in their entirety.

The present invention relates to a process for producing alkali metal alkoxides in countercurrent by reactive rectification, wherein the alkali metal is selected from sodium and potassium. The process is carried out in at least one reaction column and at least one rectification column. The process is characterized in that the heating vapour utilized for operating the column and thus for carrying out the process is condensed and the energy in the condensate obtained is used.

1. BACKGROUND OF THE INVENTION

The production of alkali metal alkoxides is an important industrial process.

Alkali metal alkoxides are used as strong bases in the synthesis of numerous chemicals, for example in the production of pharmaceutical or agrochemical active ingredients. Alkali metal alkoxides are also used as catalysts in transesterification and amidation reactions.

Alkali metal alkoxides (MOR) are produced by reactive distillation of alkali metal hydroxides (MOH) and alcohols (ROH) in a countercurrent distillation column, wherein the water of reaction formed according to the following reaction <1> is removed with the distillate.

$$MOH + ROH \rightleftharpoons MOR + H_2O$$

Such a process principle is described, for example, in U.S. Pat. No. 2,877,274 A, wherein aqueous alkali metal hydroxide solution and gaseous methanol are driven in countercurrent into a rectification column. This process is described again in generally unchanged form in WO 01/42178 A1.

Similar processes, which, however, additionally employ an entraining agent such as benzene, are described in GB 377,631 A and U.S. Pat. No. 1,910,331 A. The entraining agent here serves to separate water from the water-soluble alcohol, and the condensate is subjected to phase separation in order to separate off the water of reaction.

Correspondingly, DE 96 89 03 C describes a process for continuous production of alkali metal alkoxides in a reaction column, wherein the water-alcohol mixture withdrawn at the top of the column is condensed and then subjected to a phase separation. The aqueous phase is discarded and the alcoholic phase is returned to the top of the column together with the fresh alcohol. EP 0 299 577 A2 describes a similar process, wherein the water in the condensate is separated off with the aid of a membrane.

The most industrially important alkali metal alkoxides are those of sodium and potassium, especially the methoxides and ethoxides. Their synthesis is frequently described in the prior art, for example in EP 1 997 794 A1.

The syntheses of alkali metal alkoxides by reactive rectification described in the prior art typically afford vapours comprising the employed alcohol and water. It is advantageous for economic reasons to reuse the alcohol comprised in the vapours as a reactant in the reactive distillation. The vapours are therefore typically supplied to a rectification column and the alcohol present therein is separated off (described for example in GB 737 453 A and U.S. Pat. No. 4,566,947 A). The thus recovered alcohol is then supplied to the reactive distillation as a reactant for example. Alternatively or in addition a portion of the alcohol vapour may be utilized for heating the rectification column (described in WO 2010/097318 A1). However, this requires that the vapour be compressed in order to achieve the temperature level required for heating the rectification column.

The energy required for operating the process is normally introduced by means of heating vapour into the process of the invention, for example via heat exchangers such as vaporizers at the bottom of the column or for heating the alcohol or alkali metal hydroxide solution. In the transfer of energy, the heating vapour condenses and the resulting liquid phase, namely the heating vapour condensate, frequently still contains considerable amounts of residual heat. This results in the following disadvantages: Firstly, it is energetically undesirable for this energy to be allowed to dissipate unutilized. In addition, condensates are usually collected in a condensate network in an industrial context (chemical facilities and technology parks). When this network is fed from different plants, the condensates introduced differ in terms of temperature and pressure. In order to prevent pressure pulses in the condensate network, each plant connected to the network therefore has to actively cool the corresponding condensate, which in turn requires additional energy expenditure.

It was accordingly an object of the present invention to provide a process for producing alkali metal alkoxides which alleviates the abovementioned disadvantages and in particular allows efficient utilization of the energy in the heating vapour condensates. Apart from the advantageous saving of energy, this should also allow the condensate to be set to particular pressure and temperature values easily and energy-efficiently.

A process which achieves this object has now surprisingly been found.

2. BRIEF SUMMARY OF THE INVENTION

The present invention accordingly provides a process according to claim 1.

3. FIGURES

FIG. 1 shows a process which is not according to the invention for producing alkali metal alkoxides using various heat exchangers.

Such a plant comprises a reaction column $RR_A$<1A>. At the top of the reaction column $RR_A$<1A>, an aqueous NaOH solution is introduced as feed stream $S_{AE2}$<1A2>. As an alternative, it is also possible to introduce a methanolic NaOH or KOH solution as feed stream $S_{AE2}$<1A2> in order then to produce the corresponding sodium or potassium methoxide. Energy can optionally be introduced into the feed stream $S_{AE2}$<1A2> via a heat exchanger WT<WA5>, for example in order to preheat this feed stream. Above the bottom of the reaction column $RR_A$<1A>, methanol is introduced in vapour form as feed stream $S_{AE1}$<1A1>. Energy can optionally be introduced into the feed stream $S_{AE1}$<1A1> via a heat exchanger WT<WA4>, for example in order to preheat this feed stream. The reaction of the two feed streams $S_{AE1}$<1A1> and $S_{AE2}$<1A2> results in formation in the reaction column $RR_A$<1A> of a crude product mixture $RP_A$<1A3> which comprises $NaOCH_3$, water, $CH_3OH$, NaOH when $S_{AE2}$<1A2> comprises NaOH. When $S_{AE2}$<1A2> comprises KOH, a crude product mixture $RP_A$<1A3> comprising $KOCH_3$, water, $CH_3OH$ and KOH is obtained.

At the bottom of the reaction column $RR_A$<1A>, the product stream $S_{AS}$<1A4> which comprises sodium methoxide or potassium methoxide dissolved in methanol is obtained. The concentration of the sodium or potassium methoxide solution $S_{AS}$<1A4> can be set to the desired value by means of the optional bottom vaporizer $VS_{RRA}$<WA1> at the bottom of the column $RR_A$<1A>. Energy can optionally be transferred by means of the optional bottom vaporizer $VS_{RRA}$<WA2> to part of $S_{AS}$<1A4> which is recirculated to the reaction column $RR_A$<1A>. $VS_{RRA}$<WA2> also serves, in particular, for starting up the column $RR_A$<1A>. The optional intermediate vaporizer $VZ_{RRA}$<WA3> offers an opportunity to transfer energy to the crude product mixture $RP_A$<1A3>. This is taken off from the column $RR_A$<1A> as stream $S_{RRAZ}$<1A7>, the stream $S_{RRAZ}$<1A7> is heated in the intermediate vaporizer $VZ_{RRA}$<WA3> and then returned to the column $RR_A$<1A>.

A vapour stream $S_{AB}$<1A5> is taken off at the top of the reaction column $RR_A$<1A>. Part of the vapour stream $S_{AB}$<1A5> can be condensed in a condenser $K_{RRA}$ at the top of the reaction column $RR_A$<1A> and returned in liquid form as runback to the top of the reaction column $RR_A$<1A>. However, this embodiment which is not shown in FIG. 1, namely the setting of the runback at the top of the reaction column $RR_A$<1A>, is optional.

The vapour stream $S_{AB}$<1A5> is optionally conveyed via a heat exchanger WT<WA6> and via a compressor $VD_{31}$<11> to a rectification column $RD_A$<2>. A mixture $G_A$<21> which comprises water and methanol is obtained in the rectification column $RD_A$<2> and is separated in $RD_A$<2> into a vapour stream $S_{DAB}$<24> comprising methanol and a bottom stream $S_{DAS}$<22> comprising water and ROH. At the bottom of the column $RD_A$<2>, the vapour stream $S_{DAS}$<22> is discharged at an offtake point $E_{AK}$<42> and can partly be recirculated again via the optional bottom vaporizer $VS_A$<W7> or the bottom vaporizer $VS_A$<W8> to the column $RD_A$<2>.

At the top of the rectification column $RD_A$<2>, methanol vapour $S_{DAB}$<24> is discharged at an offtake point $E_{AK}$<41>. This is then optionally conveyed via the compressor <12> and recirculated to the reaction column $RR_A$<1A> where it is introduced as feed stream $S_{AE1}$<1A1>. The compressor <12> can also be used instead of the compressor $VD_{31}$<11>.

The intermediate vaporizer $VZ_A$<W9> offers a possibility of transferring energy to the mixture $G_A$<21>. This is taken off from the column $RD_A$<2> as stream $S_{AZ}$<23>, the stream $S_{AZ}$<23> is heated in the intermediate vaporizer $VZ_A$<W9> and then recirculated to the column $RD_A$<2>.

A stream of fresh methanol <25> can be supplied to the system via the rectification column $RD_A$<2>. Energy can be introduced into this stream via a heat exchanger WT<W10>. The fresh methanol can be introduced directly into the rectification column $RD_A$<2>.

Energy is transferred by means of the bottom vaporizer $VS_A$<W8> to part of $S_{DAS}$<22> which is recirculated to the rectification column $RD_A$<1A>. The bottom vaporizer $VS_A$<W8> here also serves, in particular, for starting up the column $RD_A$<2>. FIG. 1 shows, for the bottom vaporizer $VS_A$<W8>, the heating by means of heating vapour $H_1$<84> according to the prior art. Accordingly, energy is transferred from heating vapour $H_1$<84> via the bottom vaporizer $VS_A$<W8> to recirculated $S_{DAS}$<22> and thus ultimately made available for separation of the mixture $G_A$<21> by distillation.

The condensation temperature of the heating vapour $H_1$<84> has to be set according to the required heating power for the distillation. Since the temperature or the pressure of the heating vapour $H_3$<83> available in industrial plants is usually different from the values desired in the specific case, $H_3$<83> firstly has to be depressurized to $H_1$<84>, which occurs by means of a regulating valve <85>. This occurs with dissipation of parts of the energy present in the heating vapour $H_3$<83>.

As a result of the transfer of energy from $H_1$<84> to $S_{DAS}$<22> in the bottom vaporizer $VS_A$<W8>, $H_1$<84> condenses at least partially to form the condensate $K_1$<81> which is collected in a condensate vessel <86> where condensates <88> from other heat exchangers of the plant as shown in FIG. 1 or even other plants (e.g. in integrated sites) are optionally collected. The collected condensates then have to be disposed of as condensate stream <87> or can, for instance, be fed into the condensate network in chemical facilities. As a result, not only is part of the energy present in the condensates discarded unutilized, but it is in many cases also necessary to set these condensates to a particular temperature with additional energy consumption in order to avoid pressure pulses in the condensate network.

This problem arises not only in the case where the heating vapour $H_1$<84> heats the bottom vaporizer $VS_A$<W8>. In plants which correspond to that in FIG. 1, but in which energy of heating vapour $H_3$<83> is instead to be introduced via or in addition to the bottom vaporizer $VS_A$<W8> via another heat exchanger, the same problem arises.

Figure 2:
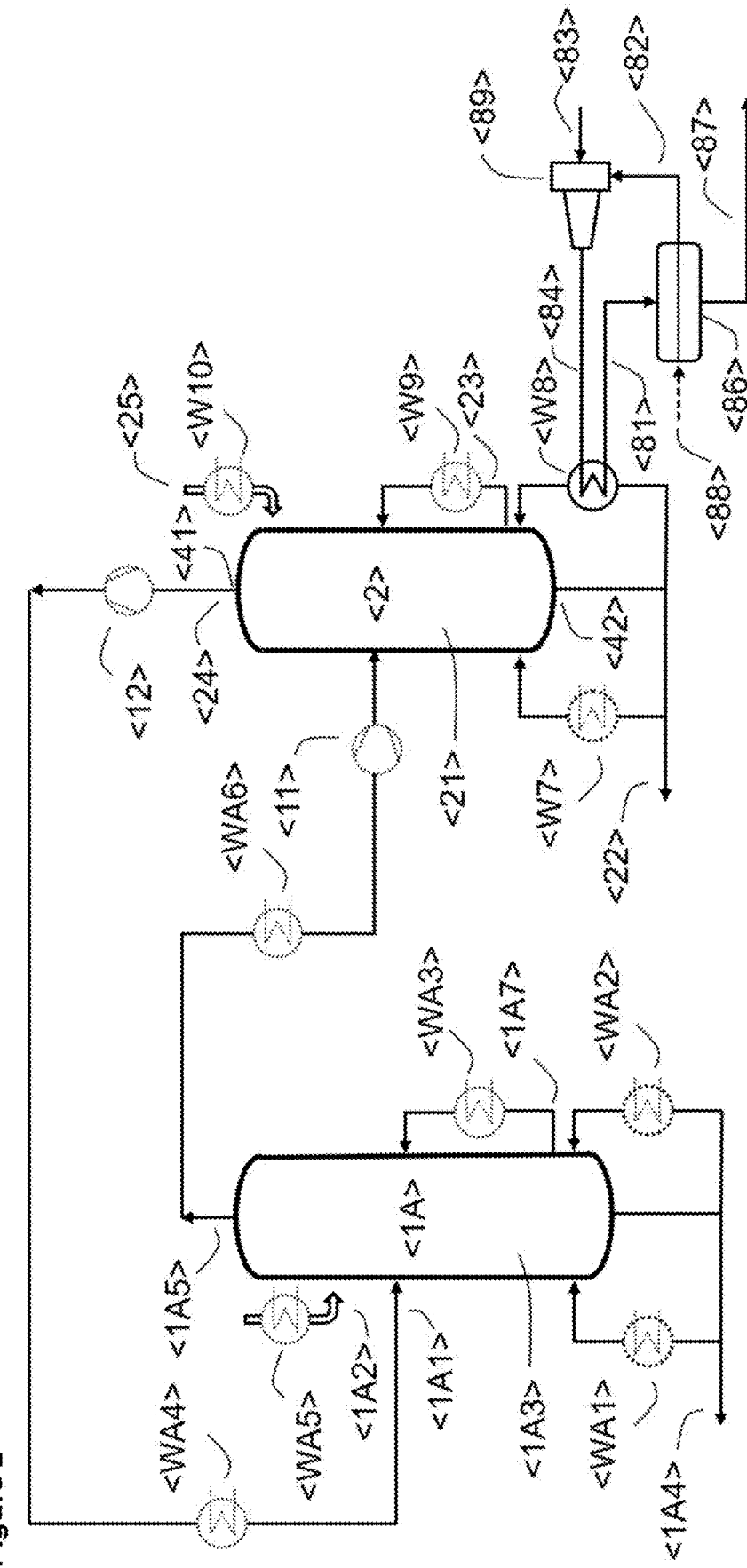

FIG. 2 shows an embodiment of the process of the invention. The plant corresponds to that described in FIG. 1. The characteristic feature of the process of the invention is illustrated with the aid of the bottom vaporizer $VS_A$<W8>. However, the heating vapour $H_1$ can, as an alternative or in addition, also be conveyed to one of the other heat exchangers WT<WA1> to <WA6>, <W7>, <W9>, <W10>.

According to the procedure in the prior art, energy is also transferred from heating vapour $H_1$<84> to $S_{DAS}$<22> via the bottom vaporizer $VS_A$<W8> and thus ultimately made available to the separation of the mixture $G_A$<21> by distillation. This gives a heating vapour condensate $K_1$<81> which is collected and depressurized in the condensate vessel <86>, optionally together with other condensates <88>. The condensates <88> can arise from heating by means of one or the other heat exchangers WT<WA1> to <WA6>, <W7>, <W9>, <W10>, when the plant comprises such a heat exchanger, or, when the process of the invention is carried out in the vicinity of another plant in which heating vapour condensate is obtained, can be conveyed from such a plant into the condensate vessel <86>. The critical difference from the processes of the prior art is that at least part of the heating vapour condensate $K_1$<81> is depressurized and a heating vapour $H_2$<82> which has a pressure $p_2$ which is lower than the pressure $p_1$ of $H_1$<84> is thus obtained. The resultant heating vapour $H_2$<82> is then mixed with fresh heating vapour $H_3$<83> having a pressure $p_3$ which is >$p_2$, where, in the embodiment of FIG. 2, $p_3$ is also >$p_1$. In this way, the heating vapour/condensate/heating vapour circuit of $H_1$<84>/$K_1$<81>/$H_2$<82> is completed and new heating vapour $H_4$, which is identical to the heating vapour $H_1$<84> with the desired pressure (and thus the desired temperature)

is obtained and can be used again in the next round as heating vapour $H_1$<84> for heating the bottom vaporizer $VS_A$<W8>.

Compared to the processes of the prior art, the following advantages are obtained thereby:

A higher proportion of the energy in the condensate $K_1$ is integrated into the process.

As a result of the energy in the condensate $K_1$ being utilized, the condensate $K_1$ has to be cooled to a lesser degree before it is fed into the condensate network in order to decrease the probability of pressure pulses in the condensate network. This saves additional cooling energy.

Figure 3:
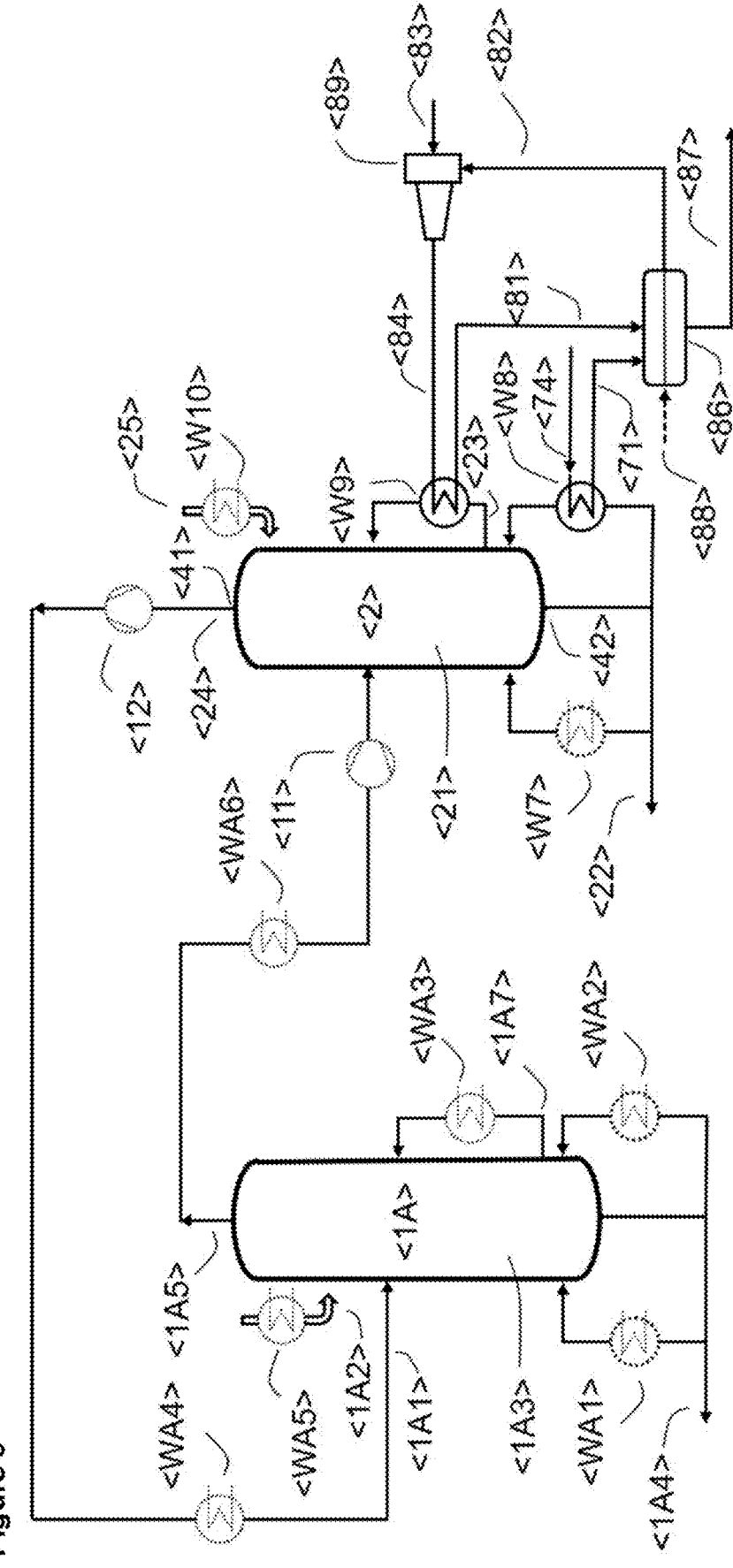

FIG. 3 shows a further embodiment of the process of the invention. This corresponds to the embodiment described in FIG. 2 except that energy is transferred from $H_1$<84> to the mixture $G_A$<21> in the intermediate vaporizer $VZ_A$<W9> on the rectification column $RD_A$<2>. In addition, the condensate vessel <86> is also supplied with hot steam condensate <71> which is obtained by condensation of heating vapour <74> during operation of the bottom vaporizer $VS_A$<W8>.

Figure 4:
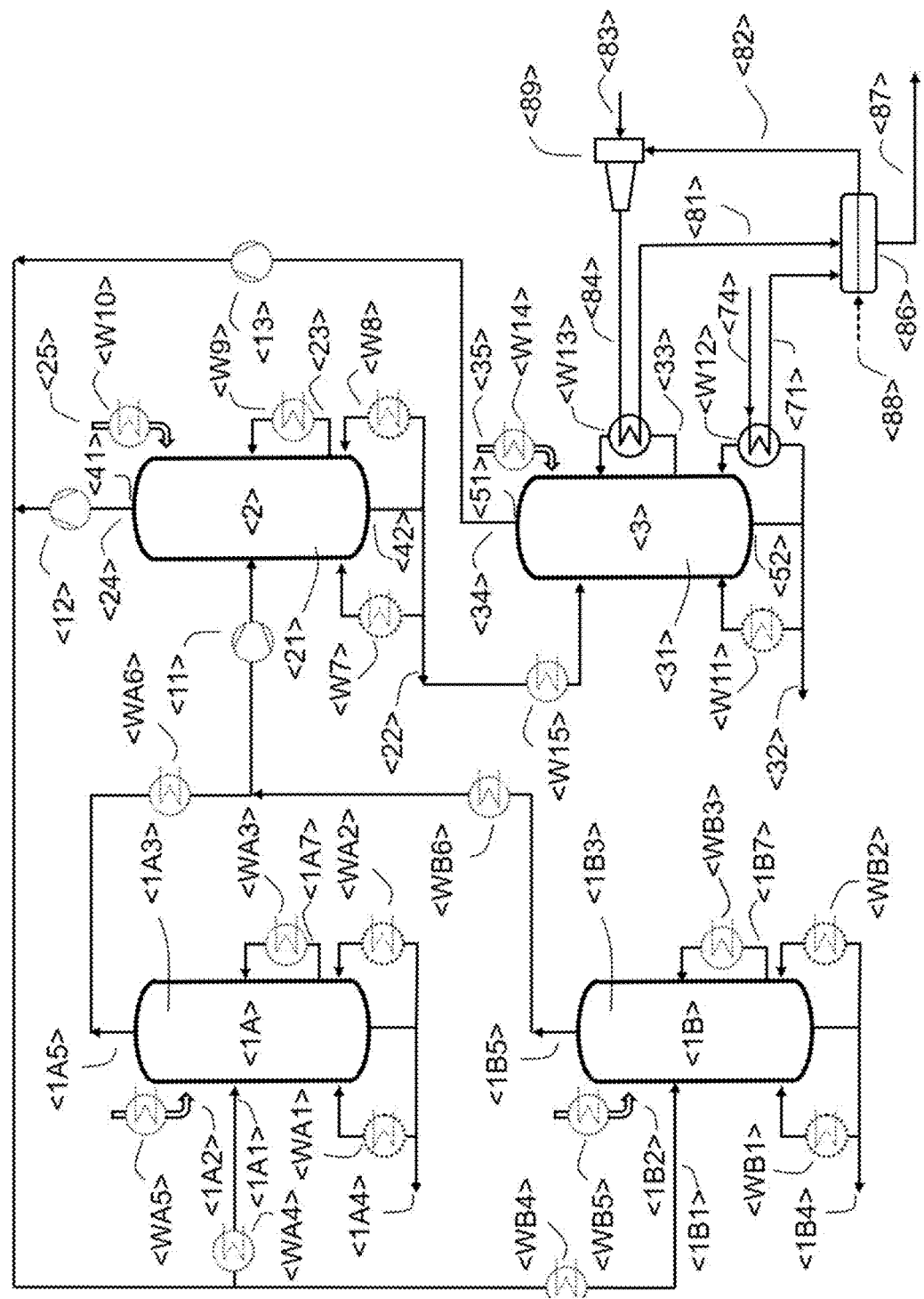

FIG. 4 shows a further embodiment of the process of the invention. This comprises the reaction column $RR_A$<1A> described in FIG. 3 and also the rectification column $RD_A$<2>. In addition, the embodiment of FIG. 4 has the following features:

Apart from the reaction column $RR_A$<1A>, the plant used in the process comprises a further reaction column $RR_B$<1B> into which an aqueous KOH solution is introduced as feed stream $S_{BE2}$<1B2>. It is also possible to employ the aqueous or alcoholic solution of NaOH, but $S_{BE2}$<1B2> is advantageously selected so that the alkali metal present in this stream differs from that in $S_{AE2}$<1A2>. Energy can optionally be introduced into the feed stream $S_{BE2}$<1B2> via a heat exchanger WT<WB5>, for example in order to preheat this feed stream. When $S_{BE2}$<1B2> comprises NaOH, $S_{BE2}$<1B2> is reacted in $RR_B$<1B> with a stream $S_{BE1}$<1B1> which comprises $CH_3OH$ and has optionally been preheated by means of the heat exchanger WT<WB4> to give a crude product mixture $RP_B$<1B3> comprising $NaOCH_3$, water, $CH_3OH$, NaOH. When $S_{BE2}$<1B2> comprises KOH, a crude product mixture $RP_B$<1B3> comprising $KOCH_3$, water, $CH_3OH$ and KOH is obtained. In this embodiment, ROH is thus methanol.

At the bottom of the reaction column $RR_B$<1B>, the product stream $S_{BS}$<1B4> comprising sodium methoxide or potassium methoxide dissolved in methanol is obtained. The concentration of the sodium or potassium methoxide solution $S_{BS}$<1A4> can be set to the desired value using the optional bottom vaporizer $VS_{RRB}$<WB1> at the bottom of the column $RR_B$<1B>. Energy can optionally be transferred by means of the optional bottom vaporizer $VS_{RRB}$<WB2> to part of $S_{BS}$<1B4> which is recirculated to the reaction column $RR_B$<1B>. $VS_{RRB}$<WB2> here also serves, in particular, for starting up the column $RR_B$<1B>. The optional intermediate vaporizer $VZ_{RRB}$<WB3> here offers an opportunity for transferring energy to the crude product mixture $RP_B$<1B3>. This is taken off from the column $RR_B$<1B> as stream $S_{RRB2}$<1B7>, the latter is heated in the optional intermediate vaporizer $VZ_{RRB}$<WB3> and then recirculated to the column $RR_B$<1B>.

At the top of the reaction column $RR_A$<1B>, a vapour stream $S_{BB}$<1B5> is taken off. Part of the vapour stream $S_{AB}$<1B5> can be condensed in a condenser at the top of the reaction column $RR_B$<1B> and returned in liquid form as runback to the top of the reaction column $RR_B$<1B>. However, this embodiment which is not shown in FIG. 4, i.e. setting of the runback at the top of the reaction column $RR_B$<1B>, is optional.

The vapour stream $S_{BB}$<1B5> is optionally conveyed via a heat exchanger WT<WB6>. $S_{BB}$<1B5> is combined with the stream $S_{AB}$<1A5> and then, after the combined stream has been conveyed via a compressor $VD_{31}$<11>, fed to a rectification column $RD_A$<2>. The two streams $S_{AB}$<1A5> and $S_{BB}$<1B5> can also be conveyed separately into the rectification column $RD_A$<2> and only be combined in the latter.

The distillation separation of the mixture $G_A$<21> into a vapour stream $S_{DAB}$<24> comprising ROH and a bottom stream $S_{DAS}$<22> comprising water and ROH takes place in the rectification column $RD_A$<2>. The bottom stream $S_{DAS}$<22> is discharged at an offtake point $E_{AK}$<42> at the bottom of the column $RD_A$<2> and can be partly recirculated via the optional bottom vaporizer $VS_A$<W7> or the bottom vaporizer $VS_A$<W8> at the bottom of the column $RD_A$<2> back to the column $RD_A$<2>. The bottom vaporizer $VS_A$<W8> here also serves, in particular, for starting up the column $RD_A$<2>.

At the top of the rectification column $RD_A$<2>, methanol vapour $S_{DAB}$<24> is discharged at an offtake point $E_{AK}$<41>. This is then optionally conveyed through the compressor <12> and recirculated to the reaction column $RR_A$<1A> where it is used as feed stream $S_{AE1}$<1A1> or $S_{BE1}$<1B1>. The compressor <12> can also be used instead of the compressor $VD_{31}$<11>.

The intermediate vaporizer $VZ_A$<W9> offers an opportunity for transferring energy to the mixture $G_A$<21>. This is taken off as stream $S_{AZ}$<23> from the column $RD_A$<2>, the stream $S_{AZ}$<23> is heated in the intermediate vaporizer $VZ_A$<W9> and then recirculated to the column $RD_A$<2>.

A stream of fresh methanol <25> can be supplied to the system via the rectification column $RD_A$<2>. Energy can be introduced into this via a heat exchanger WT<W10>. The fresh methanol <25> can be introduced directly into the rectification column $RD_A$<2>.

$S_{DAS}$<22> is optionally conveyed via a heat exchanger WT<W15> to a rectification column $RD_X$<3>. A mixture $G_X$<31> comprising water and methanol is thereby formed in $RD_X$<3>.

The distillative separation of the mixture $G_X$<31> into a vapour stream $S_{XB}$<34> comprising ROH and a bottom stream $S_{XS}$<32> comprising water and ROH takes place in the rectification column $RD_X$<3>. The bottom stream $S_{XS}$<32> is taken off at the offtake point $E_{XS}$<52> and discharged. At the bottom of the column $RD_X$<3>, the bottom stream $S_{XS}$<32> can partly be recirculated either via the optional bottom vaporizer $VS_X$<W11> or the optional bottom vaporizer $VS_X$<W12> to the column $RD_X$<3>. Energy can optionally be transferred by the optional bottom vaporizer $VS_X$<WA2> to part of $S_{XS}$<32> which is recirculated to $RD_X$<3>. $VZ_X$<W12> here also serves, in particular, for starting up the column $RD_X$<3>.

At the top of the rectification column $RD_X$<3>, methanol vapour $S_{XB}$<34> is taken off at an offtake point $E_{XK}$<51> and discharged. This vapour is then optionally conveyed via the compressor <13> and mixed with $S_{DAB}$<24> and then recirculated to the reaction columns $RR_A$<1A> and $RR_B$<1B> and used as feed stream $S_{AE1}$<1A1> or $S_{BE1}$<1B1>.

The intermediate vaporizer $VZ_X$<W13> offers an opportunity for transferring energy to the mixture $G_X$<31>. This mixture is taken off from the column $RD_X$<3> as stream $S_{XZ}$<33>, the latter is heated in $VZ_X$<W13> and then recirculated to the column $RD_X$<3>.

A stream of fresh methanol <35> can be fed to the system via the rectification column $RD_X$<3>. Energy can be introduced into this stream by means of a heat exchanger WT<W14>. The fresh methanol <35> can here by introduced directly into the rectification column $RD_X$<3>.

Energy of heating vapour $H_1$<84> is transferred via the intermediate vaporizer $VZ_X$<W13> to $S_{XS}$<32> and thus ultimately made available for the distillative separation of the mixture $G_X$<31>. This results in a heating vapour condensate $K_1$<81> which can be collected in a condensate vessel <86>, optionally together with other condensates <88>. The condensates <88> can arise from the heating by means of one of the other heat exchangers <WA1> to <WA6>, <W7>, <W9>, <W10>, if the plant has such a heat exchanger, or, when the process of the invention is carried out in the vicinity of a corresponding plant in which the heating vapour condensate is obtained, be conveyed from such a plant into the condensate vessel <86> (stream <88>). In FIG. 4, a condensate <71> which arises from the heating of the bottom vaporizer $VS_X$<W12> by means of heating vapour <74> is likewise collected in the condensate vessel <86>.

At least part of the condensate in the collection vessel <86> is depressurized and vaporized to give further heating vapour $H_2$<82>, the pressure $p_2$ of which is less than the pressure $p_1$ of $H_1$<84>. The resulting heating vapour $H_2$<82> is then mixed with fresh heating vapour $H_3$<83>, the pressure $p_3$ of which is >$p_1$ and $p_3$ is thus also >$p_2$. The heating vapour/condensate/heating vapour circuit of $H_1$<84>/$K_1$<81>/$H_2$<82> is thus completed and new heating vapour $H_4$ is obtained which is identical to the heating vapour $H_1$<84> with the desired pressure (and thus the desired temperature) and can be reused in the fresh round as heating vapour $H_1$<84> for heating the intermediate vaporizer $VZ_X$<W13>.

Figure 5:
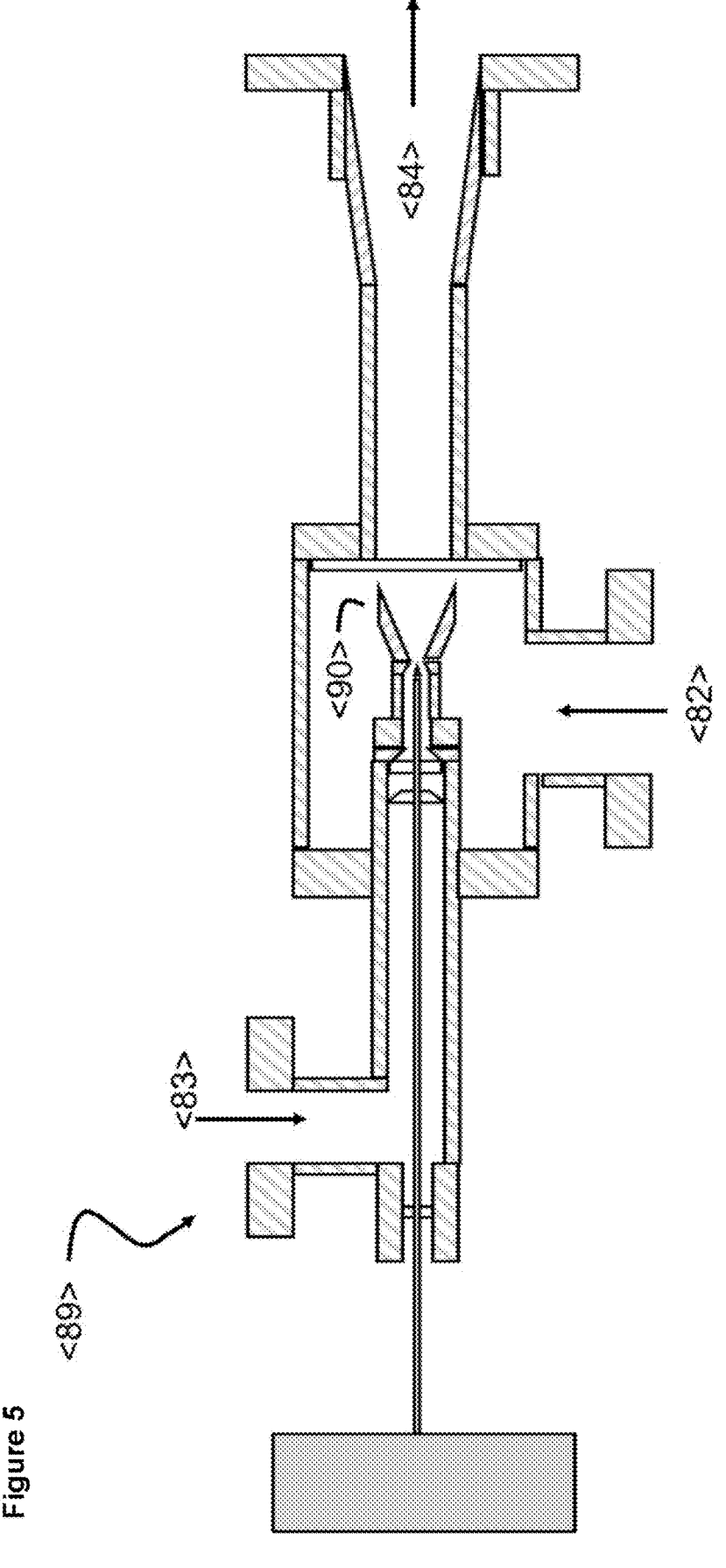

FIG. 5 shows the schematic structure of a vapour ejector DS <89>. The driving vapour $H_3$<83> is here the heating vapour, in particular the intermediate pressure vapour from the vapour network. The suction vapour $H_2$<82> is, in particular, the low-pressure vapour from the condensate vessel <86>. The two are mixed via the regulating unit <90> and conveyed via the outlet as mixed steam $H_4$<84> to the appropriate heat exchanger WT, e.g. <W8>, <W9>, <W13>. The amount of driving vapour and suction vapour can be set via the regulating unit <90>, so that pressure and thus the condensation temperature of the mixed steam $H_4$<84> can be set.

4. DETAILED DESCRIPTION OF THE INVENTION

4.1 Step (a1) of the Process According to the Invention

In step (a1) of the process according to the invention, a feed stream $S_{AE1}$ comprising ROH is reacted with a feed stream $S_{AE2}$ comprising $M_AOH$ in countercurrent in a reactive rectification column $RR_A$ to afford a crude product mixture $RP_A$ comprising $M_AOR$, water, ROH, $M_AOH$.

According to the invention, a "reactive rectification column" is a rectification column in which the reaction according to step (a1) or step (a2) of the process of the invention proceeds at least in some parts. It may also be abbreviated to "reaction column".

In step (a1) of the process according to the invention, a bottom product stream $S_{AS}$ comprising ROH and $M_AOR$ is withdrawn at the lower end of $RR_A$. A vapour stream $S_{AB}$ comprising water and ROH is withdrawn at the upper end of $RR_A$.

"Vapour stream" means that the respective stream is a gaseous stream.

In the process according to the invention, R is a $C_1$-$C_6$-hydrocarbon radical, preferably selected from the group consisting of methyl, ethyl, n-propyl, isopropyl, n-butyl, sec-butyl, isobutyl, tert-butyl, isomers of pentyl such as n-pentyl, more preferably selected from the group consisting of methyl, ethyl, n-propyl, isopropyl, yet more preferably selected from the group consisting of methyl and ethyl. R is particularly preferably methyl and ROH is accordingly methanol.

$M_A$ is selected from sodium, potassium, preferably sodium.

The feed stream $S_{AE1}$ comprises ROH. In a preferred embodiment, the proportion by mass of ROH in $S_{AE1}$ is, based on the total mass of the feed stream $S_{AE1}$, ≥95% by weight, even more preferably 99% by weight, where $S_{AE1}$ additionally comprises, in particular, water.

The alcohol ROH used as feed stream $S_{AE1}$ in step (a1) of the process of the invention can also be a commercial alcohol having a proportion by mass of alcohol, based on the total mass of the feed stream $S_{AE1}$, of more than 99.8% by weight and a proportion by mass of water, based on the total mass of the feed stream $S_{AE1}$, of up to 0.2% by weight.

The feed stream $S_{AE1}$ is preferably introduced in vapour form.

The feed stream $S_{AE2}$ comprises $M_AOH$, preferably in a proportion by mass of from 10 to 75% by weight, more preferably from 20 to 55% by weight, more preferably 48.5% by weight, in each case based on the total mass of the stream $S_{AE2}$. In a preferred embodiment, $S_{AE2}$ comprises not only $M_AOH$ but also at least one further compound selected from water, ROH. $S_{AE2}$ more preferably comprises water in addition to $M_AOH$, in which case $S_{AE2}$ is then an aqueous solution of $M_AOH$.

Step (a1) of the process of the invention is carried out in a reactive rectification column $RR_A$. Step (a2) of the process of the invention is carried out in a reactive rectification column $RR_B$.

The reaction column $RR_A$ or $RR_B$ preferably contains internals. Suitable internals are, for example, trays, structured packings or unstructured packings. When the reaction column $RR_A$ or $RR_B$ contains trays, then bubble cap trays, valve trays, tunnel trays, Thormann trays, cross-slit bubble cap trays or sieve trays are suitable. When the reaction column $RR_A$ or $RR_B$ contains trays, then preference is given to choosing trays in the case of which not more than 5% by weight, more preferably less than 1% by weight, of the liquid trickles through the respective trays. The constructional measures required to minimize trickle-through of the liquid are familiar to those skilled in the art. In the case of valve trays, particularly tightly closing valve designs are selected for example. Reducing the number of valves also makes it possible to increase the vapour velocity in the tray openings to twice the value typically established. When sieve trays are used, it is particularly advantageous to reduce the diameter of the tray openings and maintain the number of openings.

When using structured or unstructured packings, structured packings are preferred in terms of uniform distribution of the liquid.

For columns comprising unstructured packings, especially comprising random packings, and for columns comprising structured packings, the desired characteristics of the liquid distribution may be achieved when the liquid trickling density in the edge region of the column cross section adjacent to the column shell, corresponding to about 2% to 5% of the total column cross section, is reduced compared to the other cross-sectional regions by up to 100%, preferably by 5% to 15%. This can easily be achieved by, for example, targeted distributions of the drip points of the liquid distributors or the holes thereof.

In order to avoid droplet entrainment, the columns can additionally comprise appropriate internals known to those skilled in the art, for example knitted wire droplet precipitators. Examples of such droplet precipitators, for example those marketed under the name "KnitMesh V-MISTER™-Technology" by Sulzer, are described in the brochure "Gas/Liquid Separation Technology" E10508 en 4.2018, Copyright © Sulzer Ltd 2018, which can be found online at: https://www.sulzer.com/-/media/files/products/separation-technology/feed-inlet-devices/gas_liquid_separation_technology.ashx?la=en.

The process according to the invention may be carried out either continuously or discontinuously. It is preferably carried out continuously.

According to the invention, "Reaction of a feed stream $S_{AE1}$ comprising ROH with a feed stream $S_{AE2}$ comprising $M_AOH$ in countercurrent" is achieved, in particular, as a result of the feed point for at least part of the feed stream $S_{AE1}$ comprising ROH in step (a1) being located on the reaction column $RR_A$ below the feed point of the feed stream $S_{AE2}$ comprising $M_AOH$.

The reaction column $RR_A$ preferably comprises at least 2, in particular 15 to 40, theoretical plates between the feed point of the feed stream $S_{AE1}$ and the feed point of the feed stream $S_{AE2}$.

In particular, the feed stream $S_{AE1}$ comprising ROH is introduced in vapour form in the lower region of the reaction column $RR_A$. Step (a1) of the process according to the invention also encompasses the case where a portion of the feed stream $S_{AE1}$ comprising ROH is added in vapour form below the feed point of the feed stream $S_{AE2}$ comprising aqueous sodium hydroxide solution $M_AOH$ but nevertheless at the upper end or in the region of the upper end of the reaction column $RR_A$. This makes it possible to reduce the dimensions of the lower region of the reaction column $RR_A$. When part of the feed stream $S_{AE1}$ comprising ROH, in particular methanol, is introduced, in particular in vapour form, at the upper end or in the region of the upper end of the reaction column $RR_A$, then only a partial amount of from 10 to 70% by weight, preferably from 30 to 50% by weight [in each case based on the total amount of the alcohol ROH used in step (a1)] is fed in at the lower end of the reaction column $RR_A$ and the remaining partial amount is introduced in vapour form as a single stream or distributed over a plurality of substreams, preferably from 1 to 10 theoretical plates, particularly preferably from 1 to 3 theoretical plates, below the point of addition of the feed stream $S_{AE2}$ comprising $M_AOH$.

In the reaction column $RR_A$, the feed stream $S_{AE1}$ comprising ROH is then reacted with the feed stream $S_{AE2}$ comprising $M_AOH$ according to the reaction <1> described hereinabove to afford $M_AOR$ and $H_2O$, where these products are present in admixture with the reactants ROH and $M_AOH$ since an equilibrium reaction is concerned. Accordingly, a crude product mixture $RP_A$ which comprises ROH and $M_AOH$ in addition to the products $M_AOR$ and water is obtained in step (a1) of the process of the invention in the reaction column $RR_A$.

At the lower end of $RR_A$, the bottom product stream $S_{AS}$ ("$S_{AS}$" can also be referred to as "$S_{AP}$") comprising ROH and $M_AOR$ is then taken off.

At the upper end of $RR_A$, the alcohol stream which still contains water, referred to above as "vapor stream $S_{AB}$ comprising water and ROH", is then taken off.

The amount of the alcohol ROH present in the feed stream $S_{AE1}$ is preferably selected so that it simultaneously serves as solvent for the alkali metal alkoxide $M_AOR$ present in the bottom product stream $S_{AS}$.

In a preferred embodiment of the process of the invention, especially in cases in which $S_{AE2}$ comprises water in addition to $M_AOH$, the ratio of the total weight (masses; unit: kg) of alcohol ROH used as feed stream $S_{AE1}$ in step (a1) to the total weight (masses; unit: kg) of $M_AOH$ used as feed stream $S_{AE2}$ in step (a1) is from 2:1 to 50:1, more preferably 5:1 to 48:1, yet more preferably 10:1 to 35:1, yet still more preferably 13:1 to 30:1.

The reaction column $RR_A$ is operated with or without, preferably without, reflux.

"Without reflux" means that the vapor stream $S_{AB}$ comprising water and ROH taken off at the upper end of $RR_A$ or the vapour stream $S_{BB}$ comprising water and ROH taken off in the optional step (a2) at the upper end of $RR_B$ is fed in its entirety to the rectification column $RD_A$ according to step (b). The vapour stream $S_{AB}$ or the vapor stream $S_{AB}$ taken off in the optional step (a2) is preferably fed in vapor form to the first rectification column $RD_A$.

"With reflux" means that the vapor stream $S_{AB}$ which comprises water and ROH and is taken off at the upper end of the respective column, in step (a1) the reaction column $RR_A$, and the vapour stream $S_{BB}$ which comprises water and ROH and is taken off in the optional step (a2) from the reaction column $RR_B$ is not discharged in its entirety from $RR_A$ or $RR_B$, i.e. is not introduced in its entirety into the rectification column $RD_A$ but is instead partly fed back as runback to the respective column, in step (a1) $S_{AB}$, i.e. into the reaction column $RR_A$, and in the optional step (a2) $S_{BB}$, i.e. the reaction column $RR_B$. In the cases where such a reflux is established, the reflux ratio is preferably 0.005 to 0.99, more preferably 0.01 to 0.9, yet more preferably 0.02 to 0.34, particularly preferably 0.025 to 0.27 and very particularly preferably 0.03 to 0.24. Reflux can be established by a condenser $K_{RRA}$ being installed at the top of the respective column, in step (a1) the reaction column $RR_A$ and in the optional step (a2) a condenser $K_{RRB}$ being installed on the reaction column $RR_B$, in which condenser the vapour stream $S_{AB}$ or $S_{BB}$ is at least partially condensed and fed back to the respective column $RR_A$ or $RR_B$. Generally and in the context of the present invention, a reflux ratio is to be understood as meaning the ratio of the mass flow (kg/h) recycled to the respective column in liquid form (reflux or runback) to the mass flow (kg/h) discharged from the respective column in liquid form (distillate) or gaseous form (vapour).

In the embodiment in which a reflux is established on the reaction column $RR_A$, the alkali metal hydroxide $M_AOH$ employed in step (a1) as feed stream $S_{AE2}$ may also be at least partially mixed with the reflux stream and the resulting mixture thus supplied to step (a1).

Step (a1) of the process of the invention is, in particular, carried out at a temperature $T_{RRA}$ in the range from 45° C. to 190° C., preferably from 47° C. to 170° C., more preferably from 60° C. to 150° C., and in particular at a pressure $p_{RRA}$ of from 0.5 bar to 40 bar, preferably in the range from 0.75 bar to 20 bar, more preferably in the range from 0.9 bar to 10 bar, more preferably in the range from 1 bar to 7 bar, even more preferably from 1 bar to 5 bar.

The reaction column $RR_A$ comprises, in a preferred embodiment, at least one vaporizer which is, in particular, selected from intermediate vaporizers $VZ_{RRA}$ and bottom vaporizers $VS_{RRA}$, even more preferably at least one bottom vaporizer $VS_{RRA}$.

For the purposes of the invention, the expression "intermediate vaporizer" $VZ_{RRA}$ or $VZ_{RRB}$ refers to vaporizers which are located above the liquid phase of the respective column, in particular above the liquid phase of the reaction column $RR_A$ or $RR_B$. They are used, in particular, to vaporize crude product mixture $RP_A$ or $RP_B$.

For the purposes of the invention, the expression "bottom vaporizer" $VS_{RRA}$ and $VS_{RRB}$ refers to vaporizers which heat the liquid phase of the respective column, in particular the liquid phase of the reaction column $RR_A$ or $RR_B$. In these, bottom product stream $S_{AS}$ or $S_{BS}$ ("$S_{BS}$" can also be referred to as "$S_{BP}$") is at least partially vaporized.

A vaporizer is typically arranged outside the respective reaction column or rectification column. The mixture to be vaporized in the vaporizer is taken off from the column via an offtake or "offtake point" and fed to the at least one vaporizer.

In the case of intermediate vaporization of the crude product mixture $RP_A$ or $RP_B$ on the reaction column $RR_A$ or $RR_B$, this mixture is taken off as stream $S_{RRAZ}$ or $S_{RRBZ}$ and fed to the at least one intermediate vaporizer $VZ_{RRA}$ or $VZ_{RRB}$. The vaporized mixture, optionally with a residual proportion of liquid, is recirculated via an inlet or "addition point" back into the respective column $RR_A$ or $RR_B$. When the vaporizer is an intermediate vaporizer, i.e., in particular, is an intermediate vaporizer $VZ_{RRA}$ or $VZ_{RRB}$, the offtake via which the respective mixture is taken off and fed to the vaporizer is a side offtake and the inlet via which the respective vaporized mixture is returned to the column is a side inlet. When the vaporizer is a bottom vaporizer, i.e. heats the liquid phase or bottoms in the column, it is, in particular, a bottom vaporizer $VS_{RRA}$ or $VS_{RRB}$, so that at least part of the bottom offtake stream, in particular $S_{AS}$ or $S_{BS}$, is fed to the corresponding bottom vaporizer, vaporized and fed back into the respective column in the region of the bottom.

However, it is also possible as an alternative to provide tubes through which the appropriate heating medium, for example $H_1$ or $H_4$ flows, for example on a suitable tray when using an intermediate vaporizer or in the bottom region of the respective column. In this case, the vaporization occurs on the tray or in the bottom region of the column. However, it is preferable to arrange the vaporizer outside the respective column.

Suitable vaporizers VD which can be used as intermediate vaporizers VZ and bottom vaporizers VS are, for example, natural convection vaporizers, forced circulation vaporizers, forced circulation vaporizers with depressurization, tank vaporizers, falling-film evaporators or thin-film evaporators. A shell-and-tube arrangement or plate apparatus is usually employed as heat-transferring component for the vaporizer in the case of natural convection vaporizers and forced circulation vaporizers. When using a shell-and-tube heat exchanger, the heat transfer medium, for example $H_1$ or $H_4$, can either flow through the tubes and the mixture to be vaporized flows around the tubes or else the heat transfer medium flows around the tubes and the mixture to be vaporized flows through the tubes. In the case of a falling-film evaporator, the mixture to be vaporized is typically introduced as a thin film on the inside of a tube and the tube is heated externally. In contrast to a falling-film evaporator, a thin-film evaporator additionally comprises a rotor with wipers which distributes the liquid to be evaporated on the inner wall of the tube to form a thin film.

In addition to the abovementioned types of vaporizer, it is also possible to use any other type of vaporizer which is known to a person skilled in the art and is suitable for use in a rectification column or reaction column.

When the reaction column $RR_A$ or reaction column $RR_B$ comprises an intermediate vaporizer $VZ_{RRA}$ or $VZ_{RRB}$, preference is given to the respective intermediate vaporizer being arranged in the region of the feed point of the feed stream $S_{AE1}$ in the case of the reaction column $RR_A$ or in the region of the feed point of the feed stream $S_{BE1}$ in the case of the reaction column $RR_B$. In this way, a predominant part of the heat energy can be introduced via the intermediate vaporizer $VZ_{RRA}$ or $VZ_{RRB}$. It is thus possible for example to introduce more than 80% of the energy via the intermediate vaporizer. According to the invention, the intermediate vaporizer $VZ_{RRA}$ or $VZ_{RRB}$ is preferably arranged and/or configured so that more than 50%, in particular more than 75%, of the total energy required for the reactive rectification can be introduced by means of it.

When the reaction column $RR_A$ or reaction column $RR_B$ comprises an intermediate vaporizer $VZ_{RRA}$ or $VZ_{RRB}$, it is also advantageous for the intermediate vaporizer to be arranged so that the reaction column $RR_A$ or $RR_B$ has from 1 to 50, preferably from 1 to 40, theoretical plates below the intermediate vaporizer and has from 1 to 200, preferably from 1 to 40, theoretical plates above the intermediate vaporizer. In particular, the reaction column $RR_A$ or $RR_B$ then preferably has from 2 to 10 theoretical plates below the intermediate vaporizer and has from 20 to 50 theoretical plates above the intermediate vaporizer.

When the reaction column $RR_A$ or reaction column $RR_B$ comprises an intermediate vaporizer $VZ_{RRA}$ or $VZ_{RRB}$, it is also advantageous for the side offtake (i.e. the "offtake point $E_{RRA}$" on the reaction column $RR_A$ or the "offtake point $E_{RRB}$" on the reaction column $RR_B$) via which the crude product mixture $RP_A$ or $RP_B$ is fed to the intermediate vaporizer $VZ_{RRA}$ or $VZ_{RRB}$ and the side inlet (i.e. the "feed point $Z_{RRA}$" on the reaction column $RR_A$ or the "feed point $Z_{RRB}$" on the reaction column $RR_B$) via which the vaporized crude product mixture $RP_A$ or $RP_B$ from the intermediate vaporizer $VZ_{RRA}$ or $VZ_{RRB}$ is fed back into the respective reaction column $RR_A$ or $RR_B$ to be not more than two theoretical plates from one another, preferably positioned between the same plates of the reaction column $RR_A$ or reaction column $RR_B$. However, it is also possible for the side offtake and side inlet to be at different heights.

It is also advantageous, when the reaction column $RR_A$ or the reaction column $RR_B$ comprises an intermediate vaporizer $VZ_{RRA}$ or $VZ_{RRB}$, for the "offtake point $E_{RRA}$" on the reaction column $RR_A$ or the "offtake point $E_{RRB}$" on the reaction column $RR_B$ and the "feed point $Z_{RRA}$" on the reaction column $RR_A$ or the "feed point $Z_{RRB}$" on the reaction column $RR_B$ to be located below the feed points of $S_{AE2}$ or $S_{BE2}$.

In a preferred embodiment when using an intermediate vaporizer $VZ_{RRA}$ or $VZ_{RRB}$ in $RR_A$ or $RR_B$, the diameter of the reaction column $RR_A$ or $RR_B$ above the intermediate vaporizer $RR_A$ or $RR_B$ is greater than the diameter of the reaction column $RR_A$ or $RR_B$ below the intermediate vaporizer $VZ_{RRA}$ or $VZ_{RRB}$. This has the advantage of allowing capital expenditure savings.

In such an intermediate vaporizer $VZ_{RRA}$ or $VZ_{RRB}$, the liquid crude product mixture $RP_A$ comprising $M_AOR$, water, ROH, $M_AOH$ present in the reaction column $RR_A$ or liquid crude product mixture $RP_B$ comprising $M_BOR$, water, ROH, $M_BOH$ present in the reaction column $RR_B$ can be brought into the gaseous state.

As a result of the arrangement of one or more intermediate vaporizers $VZ_{RRA}$ in the upper region of the reaction column $RR_A$ or of one or more intermediate vaporizers $VZ_{RRB}$ in the upper region of the reaction column $RR_B$, the dimensions in the lower region of the reaction column $RR_A$ or $RR_B$ can be reduced. In the embodiment having at least one intermediate vaporizer, preferably a plurality of intermediate vaporizers $VZ_{RRA}$ or $VZ_{RRB}$, it is also possible to introduce substreams of the ROH in liquid form in the upper region of the reaction column $RR_A$ or $RR_B$.

In step (a1) of the process of the invention, a bottom product stream $S_{AS}$ comprising ROH and $M_AOR$ is taken off at the lower end of the reaction column $RR_A$.

Preference is given to the reaction column $RR_A$ having at least one bottom vaporizer $VS_{RRA}$ via which the bottom product stream $S_{AS}$ is then at least partly conveyed.

Bottom vaporizers are, according to the invention, arranged at the bottom of the reaction column $RR_A$ or $RR_B$ and are then referred to as "$VS_{RRA}$" or "$VS_{RRB}$". In such a bottom vaporizer, bottom product stream $S_{AS}$ or $S_{BS}$ present in the reaction column $RR_A$ or $RR_B$ can be conveyed and ROH can be at least partly removed therefrom, as a result of which the proportion by mass of $M_AOR$ or $M_BOR$ in the respective bottom stream can be set in a targeted manner.

The bottom product stream $S_{AS}$ taken off in step (a1) preferably has a proportion by mass of $M_AOR$ in ROH in the range from 1 to 50% by weight, preferably from 5 to 32% by weight, more preferably from 10 to 32% by weight, even more preferably from 15 to 32% by weight, in each case based on the total mass of $S_{AS}$.

The proportion by mass of residual water in $S_{AS}$ is preferably <1% by weight, preferably <0.5% by weight, more preferably <0.2% by weight, based on the total mass of $S_{AS}$.

The proportion by mass of starting material $M_AOH$ in $S_{AS}$ is preferably <1% by weight, preferably <0.5% by weight, more preferably <0.2% by weight, based on the total mass of $S_{AS}$.

4.2 Step (a2) of the Process According to the Invention (Optional)

According to the invention step (a2) is optionally performed. In the optional step (a2), which proceeds simultaneously with and spatially separately from step (a1) of the process of the invention, a feed stream $S_{BE1}$ comprising ROH is reacted with a feed stream $S_{BE2}$ comprising $M_BOH$ in countercurrent in a reactive rectification column $RR_B$ to give a crude product mixture $RP_B$ comprising $M_BOR$, water, ROH, $M_BOH$.

In the optional step (a2) of the process of the invention, a bottom product stream $S_{BS}$ comprising ROH and $M_BOR$ is taken off at the lower end of $RR_B$. A vapour stream $S_{BB}$ comprising water and ROH is withdrawn at the top end of $RR_B$.

$M_B$ is selected from sodium, potassium, preferably potassium.

The feed stream $S_{BE1}$ comprises ROH. In a preferred embodiment, the proportion by mass of ROH in $S_{BE1}$ is, based on the total mass of the feed stream $S_{BE1}$, ≥95% by weight, even more preferably ≥99% by weight, with $S_{BE1}$ otherwise comprising, in particular, water.

The alcohol ROH used as feed stream $S_{BE1}$ in the optional step (a2) of the process of the invention can also be a commercial alcohol having a proportion by mass of alcohol, based on the total mass of the feed stream $S_{BE1}$, of more than 99.8% by weight and a proportion by mass of water, based on the total mass of the feed stream $S_{BE1}$, of up to 0.2% by weight.

The feed stream $S_{BE1}$ is preferably introduced in vapour form.

The feed stream $S_{BE2}$ preferably comprises $M_BOH$ in a proportion by mass of from 10 to 75% by weight, more preferably from 20 to 55% by weight, more preferably from 48 to 52% by weight, in each case based on the total mass of the stream $S_{BE2}$. In a preferred embodiment $S_{BE2}$ comprises not only $M_BOH$ but also at least one further compound selected from water, ROH. It is yet more preferable when $S_{BE2}$ comprises water in addition to $M_BOH$, thus rendering $S_{BE2}$ an aqueous solution of $M_BOH$.

Step (a2) of the process according to the invention is performed in a reactive rectification column (or "reaction column") $RR_B$. Preferred embodiments of the reaction column $RR_B$ are described in section 4.1.

According to the invention "reaction of a feed stream $S_{BE1}$ comprising ROH with a feed stream $S_{BE2}$ comprising $M_BOH$ in countercurrent" is especially achieved as a result of the feed point for at least a portion of the feed stream $S_{BE1}$ comprising ROH in step (a2) being arranged below the feed point for the feed stream $S_{BE2}$ comprising $M_BOH$ on the reaction column $RR_B$.

The reaction column $RR_B$ preferably comprises at least 2, in particular 15 to 40, theoretical plates between the feed point of the feed stream $S_{BE1}$ and the feed point of the feed stream $S_{BE2}$.

In particular, the feed stream $S_{BE1}$ comprising ROH is introduced in vapour form in the lower region of the reaction column $RR_B$. The optional step (a2) of the process of the invention also encompasses the case of part of the feed stream $S_{BE1}$ comprising ROH being introduced in vapour form below the feed point of the feed stream $S_{BE2}$ comprising aqueous sodium hydroxide solution $M_BOH$ but at the upper end or in the region of the upper end of the reaction column $RR_B$. This makes it possible to reduce the dimensions of the lower region of the reaction column $RR_B$. When part of the feed stream $S_{BE1}$ comprising ROH, in particular methanol, is introduced, in particular in vapour form, at the upper end or in the region of the upper end of the reaction column $RR_B$, then only a partial amount of from 10 to 70% by weight, preferably from 30 to 50% by weight [in each case based on the total amount of the alcohol ROH used in the optional step (a2)] is fed in at the lower end of the reaction column $RR_B$ and the remaining partial amount is introduced in vapour form in a single stream or distributed over a plurality of substreams, preferably from 1 to 10 theoretical plates, particularly preferably from 1 to 3 theoretical plates, below the feed point of the feed stream $S_{BE2}$ comprising $M_BOH$.

In the reaction column $RR_B$ the feed stream $S_{BE1}$ comprising ROH is then reacted with the feed stream $S_{BE2}$ comprising $M_BOH$ according to the reaction <1> described hereinabove to afford $M_BOR$ and $H_2O$, where these products are present in admixture with the reactants ROH and $M_BOH$ since an equilibrium reaction is concerned. Accordingly, a crude product mixture $RP_B$ which comprises the products $M_BOR$ and water together with ROH and $M_BOH$ is obtained in the optional step (a2) of the process of the invention in the reaction column $RR_B$.

The bottom product stream $S_{BS}$ ("$S_{BS}$" can also be referred to as "$S_{BP}$") comprising ROH and $M_BOR$ is then obtained and taken off at the lower end of $RR_B$.

The alcohol stream additionally containing water, hereinafter referred to as "vapour stream $S_{BB}$ comprising water and ROH" is then taken off at the upper end of $RR_B$.

The amount of alcohol ROH present in the feed stream $S_{BE1}$ is preferably selected so that it simultaneously serves as solvent for the alkali metal alkoxide $M_BOR$ present in the bottom product stream $S_{BP}$.

In a preferred embodiment of the optional step (a2) of the process of the invention, and especially in cases in which $S_{BE2}$ comprises water in addition to $M_BOH$, the ratio of the total weight (masses; unit: kg) of alcohol ROH used as feed stream $S_{BE1}$ in step (a2) to the total weight (masses; unit: kg) of $M_BOH$ used as feed stream $S_{BE2}$ in step (a2) is from 2:1 to 50:1, more preferably 5:1 to 48:1, yet more preferably 10:1 to 35:1, yet still more preferably 13:1 to 30:1.

This vapour stream $S_{BB}$ comprising water and ROH is supplied to step (b) of the process according to the invention. It is mixed with $S_{AB}$ before being supplied to step (b) of the process of the invention or supplied separately from $S_{AB}$ to step (b) of the process of the invention. Vapour stream $S_{BB}$ is preferably mixed with $S_{AB}$ and the resulting mixed vapour stream is then introduced into step (b) of the process of the invention.

The reaction column $RR_B$ is operated with or without, preferably without, reflux.

In the embodiment in which reflux is established on the reaction column $RR_B$, the alkali metal hydroxide $M_BOH$ used as feed stream $S_{BE2}$ in the optional step (a2) can also be mixed at least partly with the reflux stream and the resulting mixture can thus be supplied to the optional step (a2).

The optional step (a2) of the process of the invention is, in particular, carried out at a temperature $T_RRB$ in the range from 45° C. to 190° C., preferably from 47° C. to 170° C., more preferably from 60° C. to 150° C., and in particular at a pressure $p_{RRB}$ of from 0.5 bar to 40 bar, preferably in the range from 0.75 bar to 20 bar, more preferably in the range from 0.9 bar to 10 bar, more preferably in the range from 1 bar to 7 bar, even more preferably from 1 bar to 5 bar.

In a preferred embodiment, the reaction column $RR_B$ comprises at least one vaporizer which is, in particular, selected from intermediate vaporizers $VZ_{RRB}$ and bottom vaporizers $VS_{RRB}$. The reaction column $RR_B$ particularly preferably comprises at least one bottom vaporizer $VS_{RRB}$.

In the optional step (a2) of the process of the invention, a bottom product stream $S_{BS}$ comprising ROH and $M_BOR$ is taken off at the lower end of the reaction column $RR_B$.

Preference is given to the reaction column $RR_B$ comprising at least one bottom vaporizer $VS_{RRB}$ via which the bottom product stream $S_{BS}$ is then at least partly conveyed.

The bottom product stream $S_BS$ taken off in step (a2) preferably has a proportion by mass of $M_BOR$ in ROH in the range from 1 to 50% by weight, preferably from 5 to 32% by weight, more preferably from 10 to 32% by weight, even more preferably from 15 to 32% by weight, in each case based on the total mass of $S_{BS}$.

The proportion by mass of residual water in $S_{BS}$ is preferably <1% by weight, preferably <0.5% by weight, more preferably <0.2% by weight, based on the total mass of $S_{BS}$.

The proportion by mass of starting material $M_BOH$ in $S_{BS}$ is preferably <1% by weight, preferably <0.5% by weight, more preferably <0.2% by weight, based on the total mass of $S_{BS}$.

In a preferred embodiment of the present process, step (a2) is carried out.

This has the advantage that two different alkali metal alkoxides can be produced without causing cross-contamination of the one alkali metal alkoxide with the other or product losses occurring on changing over of the starting material $M_AOH$ to $M_BOH$.

The optional step (a2) of the process of the invention is carried out simultaneously with and spatially separately from step (a1). Spatial separation is ensured by performing steps (a1) and (a2) in the two reaction columns $RR_A$ and $RR_B$.

In an advantageous embodiment of the invention the reaction columns $RR_A$ and $RR_B$ are accommodated in one column shell, where the column is at least partially subdivided by at least one dividing wall. Such a column having at least one dividing wall will according to the invention be referred to as "DWC". Such dividing wall columns are familiar to those skilled in the art and are described for example in U.S. Pat. No. 2,295,256, EP 0 122 367 A2, EP 0 126 288 A2, WO 2010/097318 A1 and I. Dejanović, Lj. Matijašević, Ž. Olujić, *Chemical Engineering and Processing* 2010, 49, 559-580. In the dividing wall columns suitable for the process according to the invention the dividing walls preferably extend to the column floor and, in particular, preferably span at least a quarter, more preferably at least a third, yet more preferably at least half, yet more preferably at least two thirds, yet still more preferably at least three quarters, of the column by height They divide the columns into at least two reaction spaces in which spatially separate reactions may be carried out. The reaction spaces provided by the at least one dividing wall may be of identical or different sizes.

In the regions separated by the dividing wall, the bottom product streams $S_{AS}$ and $S_{BS}$ can, in this embodiment, be taken off separately and preferably be conveyed via the bottom vaporizer $VS_{RRA}$ or $VS_{RRB}$ installed for each reaction space formed by the at least one reaction wall, in which a desired concentration of $M_AOR$ or $M_BOR$ can be set by removal of ROH from $S_{AS}$ or $S_{BS}$.

4.3 Step (b) of the Process According to the Invention

In step (b) of the process of the invention, the vapour stream $S_{AB}$ and, when step (a2) is carried out, the vapour stream $S_{BB}$, mixed with $S_{AB}$ or separately from $S_{AB}$ is introduced into a rectification column $RD_A$ so that a mixture $G_A$ comprising water and ROH is present in the rectification column $RD_A$.

In the optional form of the process of the invention in which step (a2) is carried out, the vapour stream $S_{BB}$ is preferably mixed with $S_{AB}$ and the mixed vapour obtained is then introduced into the rectification column $RD_A$.

In one embodiment of the present invention, the vapour stream $S_{AB}$ and, in cases in which the optional step (a2) is carried out, the vapour stream $S_{BB}$ can be compressed before they are introduced into the rectification column $RD_A$. This can occur by means of a compressor $VD_{31}$.

A person skilled in the art can provide one or more compressors between the columns on the basis of such a person's specialist knowledge. Particularly in the case of gaseous streams which connect two or more columns, a compression/compression step should always be provided when the pressure in the column into which a gaseous stream is fed is greater than the pressure in the column from which the stream concerned exits.

It goes without saying that even in the embodiments in which the optional step (a2) is carried out and $S_{BB}$ is introduced separately from $S_{AB}$ into the rectification column $RD_A$, $S_{AB}$ and $S_{BB}$ mix in the rectification column $RD_A$, so that a mixture $G_A$ comprising water and ROH is in every case obtained in the rectification column $RD_A$ after step (b) has been carried out.

As rectification column $RD_A$ in step (b) of the process of the invention, it is possible to use rectification columns known to a person skilled in the art. The rectification column $RD_A$ preferably contains internals. Suitable internals are, for example, trays, unstructured packings or structured packings. As trays, use is normally made of bubble cap trays, sieve trays, valve trays, tunnel trays or slit trays. Unstructured packings are generally beds of random packing elements. Packing elements normally used are Raschig rings, Pall rings, Berl saddles or Intalox® saddles. Structured packings are for example marketed under the trade name Mellapack® from Sulzer. Apart from the internals mentioned, further suitable internals are known to a person skilled in the art and can likewise be used.

Preferred internals have a low specific pressure drop per theoretical plate. Structured packings and random packing elements have, for example, a significantly lower pressure drop per theoretical plate than trays. This has the advantage that the pressure drop in the rectification column remains very low and the mechanical load on the compressor and the temperature of the alcohol/water mixture $G_A$ to be vaporized remain low.

When the rectification column $RD_A$ contains structured packings or unstructured packings these may be divided or in the form of an uninterrupted packing. However, it is usual to provide at least two packing sections, one packing section above the feed point for the vapour stream to be separated (this is $S_{AB}$ or, mixed or separately from one another, $S_{AB}$ and $S_{BB}$) and a packing section below the feed point for the vapour stream to be separated. When a packing is used, for example a bed of random packing elements, the packing elements usually rest on a suitable support system. Preference is given to an embodiment in which packings are installed in the rectification column $RD_A$ above the inlet and trays are installed below the inlet.

The rectification column $RD_A$ can also comprise internals for preventing entrainment of droplets as have been described for the reaction column $RR_A$.

In an advantageous embodiment of the invention, the reaction column $RR_A$ of step (a1), or reaction columns $RR_A$ and $RR_B$ in the above-described preferred embodiment in which step (a2) is carried out, and the rectification column $RD_A$ of step (b) for separation of the mixture $G_A$ are accommodated in a column shell, with the column being divided at least partly by at least one dividing wall, or in the above-described preferred embodiment in which step (a2) is carried out, by at least two dividing walls, with the at least one dividing wall or the at least two dividing walls extending to the bottom of the column. As described at point 4.2 this is then a dividing wall column again.

In this case, the reaction to form the crude product mixture $RP_A$ as per step (a1) or the crude product mixtures $RP_A$ and $RP_B$ as per steps (a1) and (a2) is carried out in part of the DWC, with the feed stream $S_{AE2}$ and optionally the feed stream $S_{BE2}$ being introduced below but at approximately the height of the upper end of the dividing wall and the feed stream $S_{AE1}$ and optionally the feed stream $S_{BE1}$ being introduced in vapour form at the lower end. The alcohol/water mixture formed above the feed point of the feed stream then becomes distributed above the dividing wall over the entire column region which serves as enrichment section of the rectification portion $RD_A$. The second, lower part of the column which has been separated off by the dividing wall is the stripping section of the rectification column $RD_A$. The energy required for the distillation is then supplied via a vaporizer at the lower end of the second part of the column separated off by the dividing wall, with this vaporizer being able to be heated conventionally or be heated by means of heating vapour, for example $H_1$ or $H_4$. When the vaporizer is heated conventionally, an intermediate vaporizer which can be heated by means of heating vapour, for example $H_1$ or $H_4$, can be additionally provided.

At the end of step (b) of the process of the invention, a mixture $G_A$ comprising water and ROH is finally obtained in the rectification column $RD_A$. The composition of the mixture $G_A$ is determined, in particular, by the composition of the vapour stream $S_{AB}$ or, when step (a2) is carried out, in particular proportionately by the composition of the two vapour streams $S_{AB}$ and $S_{BB}$.

4.4 Step (c) of the Process According to the Invention

In step (c) of the process of the invention, the mixture $G_A$ comprising water and ROH is separated in $RD_A$ into an ROH-comprising vapour stream $S_{DAB}$ at the upper end of $RD_A$ and a bottom stream $S_{DAS}$ comprising water and ROH at the lower end of $RD_A$.

The pressure $p_A$ in $RD_A$ can be set by a person skilled in the art on the basis of the person's specialist knowledge. It is preferably in the range from 1 bar to 20 bar, preferably from 1 bar to 15 bar, more preferably from 1 to 10 bar.

The temperature $T_A$ in $RD_A$ can be set by a person skilled in the art on the basis of such a person's specialist knowledge. It is preferably in the range from 40° C. to 220° C., preferably from 60° C. to 190° C.

The separation according to step (c) of the process of the invention is a fractional distillation of the alcohol/water mixture $G_A$ as is known to a person skilled in the art.

At the bottom (another word for "bottom" is "at the lower end") of the rectification column $RD_A$, a stream $S_{DAS}$ comprising alcohol is obtained.

At the top (another word for "top" is "at the upper end") of the rectification column $RD_A$, the vapour stream $S_{DAB}$ comprising ROH is additionally obtained. The preferred proportion by mass of ROH in this vapour stream $S_{DAB}$ is ≥99% by weight, preferably ≥99.6% by weight, more preferably 99.9% by weight, in each case based on the total mass of $S_{DAB}$, with the balance being, in particular, water.

The bottom stream $S_{DAS}$ is discharged from $RD_A$ at an offtake point $E_{AS}$ at the lower end of $RD_A$ and the vapour stream $S_{DAB}$ is discharged from $RD_A$ at an offtake point $E_{AK}$ at the upper end of $RD_A$.

For the purposes of the present invention, "offtake point $E_{AK}$ at the upper end of $RD_A$" means that $E_{AK}$ is installed on the column in such a way that the vapour stream $S_{DAB}$ is taken off as overhead stream or as side offtake stream above the internals in the rectification column $RD_A$.

For the purposes of the present invention, "offtake point $E_{AS}$ at the lower end of $RD_A$" means that $E_{AS}$ is installed on the column in such a way that the bottom stream $S_{DAS}$ is taken off as bottom stream or as side offtake stream below the internals in the rectification column $RD_A$.

In an optional embodiment of the process of the invention, at least one further stream $S_{AZ}$ which comprises ROH and water and is different from $S_{DAS}$ and $S_{DAB}$ is discharged from $RD_A$, energy is transferred to this stream and the stream is recirculated into $RD_A$, where the position of the offtake point $E_{AZ}$ on $RD_A$ is located between the two offtake points $E_{AS}$ and $E_{AK}$. The stream $S_{AZ}$ comprises the mixture $G_A$.

In this optional embodiment of step (c) of the process of the invention, it is possible to supply energy to the mixture $G_A$. In a preferred embodiment, this occurs by the mixture $G_A$ being taken off as stream $S_{AZ}$ and conveyed via an intermediate vaporizer $VZ_A$ in which energy is transferred from a heat transfer medium, in particular heating vapour $H_1$ or $H_4$ or a different heating medium $W_1$ to $S_{AZ}$ or $G_A$. This energy transfer can advantageously be carried out by the mixture $G_A$ being conveyed as stream $S_{AZ}$ and $W_1$ or the mixture $G_A$ being conveyed as stream $S_{AZ}$ and the heating vapour $H_1$ or $H_4$ being conveyed through an intermediate vaporizer $VZ_A$.

At least part of the alcohol ROH obtained in the vapour stream $S_{DAB}$ in the distillation is preferably fed to the reaction column $RR_A$ at least as part of the feed stream $S_{AE1}$ and, in the cases in which step (a2) is carried out in the process of the invention, alternately or additionally to the reaction column $RR_B$ at least as part of the feed stream $S_{BE1}$.

In step (c), the vapour $S_{AB}$ or $S_{AB}$ and $S_{BB}$ obtained in step (a1) or step (a1) and (a2) is separated by distillation. These vapours comprise essentially the alcohol ROH and water. In particular, $S_{AB}$ or $S_{AB}$ and $S_{BB}$ are each a water/alcohol mixture in which the proportion by mass of ROH is preferably in the range >80% by weight, more preferably >85% by weight, even more preferably >90% by weight (based on the total mass of $S_{AB}$ or $S_{AB}$ and $S_{BB}$). Thus, $G_A$ is in particular an alcohol/water mixture in which the proportion by mass of ROH is preferably in the range >80% by weight, more preferably >95% by weight, even more preferably >90% by weight (based on the total mass of $G_A$).

The bottom stream $S_{DAS}$ taken off in step (c) comprises ROH in a proportion by mass of, in particular, from 0.005 to 95% by weight, based on the total mass of $S_{DAS}$. Preference is given to from 25 to 95% by weight in the cases in which step (d) is carried out and from 0.005 to 3% by weight in the cases in which step (d) is not carried out, in each case based on the total mass of $S_{DAS}$. $S_{DAS}$ preferably comprises essentially water in addition to the alcohol ROH.

The alcohol ROH is consumed in the process according to the invention and especially in a continuous process mode therefore requires replacement with fresh alcohol ROH.

Fresh alcohol ROH is, in particular, introduced into at least one of the columns selected from reactive rectification column $RD_A$, reaction column $RR_A$ and, when step (a2) is carried out, alternatively or additionally into the reaction column $RR_B$ and, when step (d) is carried out, alternatively or additionally into the at least one reaction column $RD_X$.

The introduction of the fresh alcohol ROH is effected, in particular, directly as feed stream $S_{AE1}$ comprising ROH into the reaction column $RR_A$ or, in the embodiments in which step (a2) is carried out, into the reaction columns $RR_A$ and $RR_B$.

At least part of the vapour stream $S_{AB}$ taken off at the offtake point $E_{AK}$ at the upper end of the rectification column $RD_A$ is preferably fed to the reaction column $RR_A$ at least as part of the feed stream $S_{AE1}$ and, in the cases in which step (a2) is carried out in the process of the invention, alternatively or additionally to the reaction column $RR_B$ at least as part of the feed stream $S_{BE1}$.

In a further preferred embodiment in which step (d) is carried out, the vapour stream $S_{XB}$ can be used at least partly as feed stream $S_{AE1}$ in step (a1) and optionally as feed stream $S_{BE1}$ in step (a2).

In the particularly preferred embodiment in which step (d) is carried out, $S_{DAB}$ and $S_{XB}$ can be used at least partly as feed stream $S_{AE1}$ in step (a1) and optionally as feed stream $S_{BE1}$ in step (a2). $S_{DAB}$ and $S_{XB}$ can then be fed separately from one another to the respective reactive rectification column $RR_A$ or $RR_B$ or firstly be mixed with one another and then fed to the respective reactive rectification column $RR_A$ or $RR_B$. In this embodiment, $S_{DAB}$ and $S_{XB}$ are preferably firstly mixed with one another and then fed to the respective reactive rectification column $RR_A$ or $RR_B$.

In this preferred embodiment, greater preference is given to the fresh alcohol ROH being supplied to at least one of the rectification columns $RD_A$, $RD_X$, preferably both columns $RD_A$ and $RD_X$.

When the fresh alcohol ROH is supplied to the rectification column $RD_A$ or $RD_X$, it is preferably fed in either in the enrichment section of the respective rectification column or directly at the top of the respective rectification column. The optimal feed point is dependent on the water content of the fresh alcohol used and secondly on the desired residual water content in the vapour stream $RD_A$ or $RD_X$. The higher the proportion of water in the alcohol used and the higher the purity requirement in the vapour stream $S_{DAB}$ or $S_{XB}$, the more useful is an inlet of some theoretical plates below the top of the rectification column $RD_A$ or $RD_X$. Preference is given to up to 20 theoretical plates below the top of the rectification column $RD_A$ or $RD_X$, and in particular from 1 to 5 theoretical plates.

When the fresh alcohol ROH is introduced into the rectification column $RD_A$ or $RD_B$, it is introduced at temperatures up to the boiling point, preferably at room temperature. Introduction of the fresh alcohol ROH in gaseous form is also possible. Here, a dedicated inlet can be provided for the fresh alcohol

4.5 Step (d) of the Process According to the Invention (Optional)

Step (d) of the process according to the invention is optionally carried out. In the optional step (d) of the process according to the invention, $S_{DAS}$ is, in its entirety or partly, separated in at least one rectification column $RD_X$ which is different from $RD_A$ into a vapour stream $S_{XB}$ comprising ROH at the upper end of $RD_X$ and a bottom stream $S_{XS}$ comprising water and optionally ROH at the lower end of $RD_X$.

As a result, a mixture $G_X$ comprising water and ROH is present in the at least one rectification column $RD_X$ when step (d) is carried out.

The bottom stream $S_{XS}$ is discharged from the at least one rectification column $RD_X$ at an offtake point $E_{XS}$ at the lower end of the column and the vapour stream $S_{XB}$ is discharged from the at least one rectification column $RD_X$ at an offtake point $E_{XK}$ at the upper end of the column.

For the purposes of the present invention, "offtake point $E_{XK}$ at the upper end of the at least one rectification column $RD_X$" means that $E_{XK}$ is installed on the at least one rectification column $RD_X$ in such a way that the vapour stream $S_{XB}$ is taken off from the at least one rectification column $RD_X$ as overhead stream or as side offtake stream above the internals.

For the purposes of the present invention, "offtake point $E_{XS}$ at the lower end of the at least one rectification column $RD_X$" means that $E_{XS}$ is installed on the column in such a way that the bottom stream $S_{XS}$ is taken off from the at least one rectification column $RD_X$ as bottom stream or as side offtake stream below the internals.

The pressure $p_x$ in $RD_X$ can be set by a person skilled in the art on the basis of such a person's specialist knowledge. It is preferably in the range from 1 bar to 20 bar, preferably from 1 bar to 15 bar, more preferably from 1 bar to 10 bar.

The temperature $T_X$ in $RD_X$ can be set by a person skilled in the art on the basis of such a person's specialist knowledge. It is preferably in the range from 40° C. to 220° C., preferably from 60° C. to 190° C.

The feature "at least one rectification column $RD_X$ which is different from $RD_A$" means that the optional step (d) of the process of the invention encompasses the case in which the separation of the vapour stream $S_{DAS}$ is carried out in only one rectification column $RD_X$. However, it also encompasses the case where the separation of the vapour stream $S_{DAS}$ is carried out in more than one rectification column $RD_X$.

In the embodiment of the present invention in which more than one column $RD_X$ is used for the separation of $S_{DAS}$ and the column $RD_A$ is thus followed by more than one column $RD_X$, the first of these columns $RD_X$, into which the bottom stream $S_{DAS}$ from $RD_A$ is fed, is referred to as "$RD_{X1}$" and the column(s) following the column $RD_{X1}$ and into which the bottom stream from $RD_{X1}$ is fed is/are referred to as "$RD_{X2}$", etc.

Each rectification column $RD_X$ which is used in addition to the first rectification column "$RD_{X1}$" is referred to generally as "$RD_{X(n+1)}$", where n is an integer and indicates the number of the total number of rectification columns $RD_X$ beyond the rectification column $RD_{X1}$. At the same time, the integer "n" assigned to a particular column $RD_{X(n+1)}$ denotes the number of columns $RD_X$ which are located between the column $RD_{X(n+1)}$ concerned and $RD_A$.

Accordingly, in the case of a total of two columns $RD_X$ n would be 1, in the case of three columns $RD_X$ n would be 2, etc.

In the embodiments of the present invention in which more than one column $RD_X$ is used for the separation of $S_{DAS}$, a vapour stream $S_{XB1}$ comprising ROH is then obtained at the upper end of each of the rectification columns $RD_{X1}$ and a bottom stream $S_{XS1}$ comprising water and optionally ROH is obtained at the lower end of each of the rectification columns $RD_{X1}$. The mixture $G_{X1}$ comprising water and ROH is present in the rectification column $RD_{X1}$.

In each additional rectification column $RD_{X(n+1)}$, a vapour stream $S_{XB(n+1)}$ comprising ROH is then correspondingly obtained at the upper end of $RD_{X(n+1)}$ and a bottom stream $S_{XB(n+1)}$ comprising water and optionally ROH is obtained at the lower end of $RD_{X(n+1)}$. The mixture $G_{X(n+1)}$ comprising water and ROH is present in the rectification column $RD_X$ $_{(n+1)}$. "n" here is an integer having the above-described meaning.

In the embodiment of the present invention in which more than one column $RD_X$ is used for the separation of $S_{DAS}$, this separation is then carried out so that $S_{DAS}$ is separated in $RD_{X1}$ into a vapour stream $S_{XB1}$ comprising ROH at the upper end of $RD_{X1}$ and a bottom stream $S_{XS1}$ comprising water and optionally ROH at the lower end of $RD_{X1}$. In each column $RD_{X(n+1)}$ following $RD_{X1}$, the bottom stream $S_{Xsn}$ from the preceding column $RD_{Xn}$ is then separated into a vapour stream $S_{XB(n+1)}$ comprising ROH at the upper end of $RD_{X(n+1)}$ and a bottom stream $S_{XS(n+1)}$ comprising water and optionally ROH at the lower end of $RD_{X(n+1)}$.

In this embodiment, too, $S_{DAS}$ is overall separated into a vapour stream $S_{XB}$ comprising ROH [which is then composed of the individual vapour streams $S_{XB1}$ and $S_{XB(n+1)}$] and a bottom stream $S_{XS}$ comprising water and optionally ROH [which then corresponds to the bottom stream $S_{XS(n+1)}$ of the last column $RD_{X(n+1)}$].

The bottom stream $S_{DAS}$ can, in an embodiment of the present invention, be conveyed via a pump into the at least one rectification column $RD_X$. Likewise, in the case of a plurality of rectification columns $RD_X$, a pump can be used in each case in order to convey the bottom stream $S_{XSn}$ from a rectification column $RD_{Xn}$ into the rectification column $RD_{X(n+1)}$.

Rectification columns suitable as rectification column $RD_X$ are known to those skilled in the art. Preferred embodiments such as internals, etc., in $RD_X$ are those described in section 4.3 for $RD_A$.

The separation in step (d) of the process of the invention is a fractional distillation as is known to a person skilled in the art of the alcohol/water mixture $G_X$ which is obtained in the at least one rectification column $RD_X$ when the bottom stream $S_{DAS}$ is fed into the at least one rectification column $RD_X$.

If only one rectification column $RD_X$ is used, the bottom stream $S_{XS}$ taken off from the rectification columns $RD_X$ in step (d) comprises ROH in a proportion by mass of, in particular, from 0.0001 to 3% by weight, preferably from 0.005 to 1% by weight, in each case based on the total mass of $S_{XS}$. $S_{XS}$ preferably comprises essentially water in addition to the alcohol ROH.

If more than one rectification column $RD_X$ is used, the bottom stream $S_{XS(n+1)}$ which has been taken off at the bottom of the last rectification column $RD_{X(n+1)}$ comprises ROH in a proportion by mass of, in particular, from 0.0001 to 3% by weight, preferably from 0.005 to 1% by weight, in each case based on the total mass of $S_{XS}$. $S_{XS}$ preferably comprises essentially water in addition to the alcohol ROH.

At the top (another word for "top" is "at the upper end") of the at least one rectification column $RD_X$, the vapour stream $S_{XB}$ comprising ROH is additionally obtained. The preferred proportion by mass of ROH in this vapour stream $S_{XB}$ is ≥99% by weight, preferably ≥99.6% by weight, more preferably 99.9% by weight, in each case based on the total mass of $S_{XB}$, with the balance being, in particular, water.

In an optional embodiment of the process of the invention, at least one further stream $S_{XZ}$ which comprises ROH and water and is different from $S_{XS}$ and $S_{XB}$ is discharged from the at least one rectification column $RD_X$ at an offtake point $E_{XZ}$, energy is transferred to this stream and the stream is recirculated to the same at least one rectification column $RD_X$, where the position of the offtake point $E_{XZ}$ on the at least one rectification column $RD_A$ is located between the two offtake points $E_{XS}$ and $E_{XK}$. The stream $S_{XZ}$ comprises the mixture $G_X$.

In this optional embodiment of the optional step (d) of the process of the invention, it is possible to supply energy to the mixture $G_X$. In a preferred embodiment, this occurs by the mixture $G_X$ being conveyed as stream $S_{XZ}$ via an intermediate vaporizer $VZ_X$ in which energy is transferred from a heat transfer medium, in particular heating vapour $H_1$ or $H_4$ or a different heat transfer medium $W_1$ to $S_{XZ}$ or $G_X$. This energy transfer can advantageously be carried out by the mixture $G_X$ being conveyed as stream $S_{XZ}$ and $W_1$ or the mixture $G_X$ being conveyed as stream $S_{XZ}$ and the heating vapour $H_1$ or $H_4$ being conveyed via an intermediate vaporizer $VZ_X$.

At least part of the vapour stream $S_{XB}$ taken off at the offtake point $E_{XK}$ at the upper end of the at least one rectification column $RD_X$ is preferably fed to the reaction column $RR_A$ at least as part of the feed stream $S_{AE1}$ and, in the cases in which step (a2) is carried out in the process of the invention, alternatively or additionally to the reaction column $RR_B$ at least as part of the feed stream $S_{BE1}$.

When both $S_{DAB}$ and also $S_{XB}$ are introduced at least as part of the feed stream $S_{AE1}$ and, in the cases in which step (a2) is carried out in the process of the invention, alternatively or additionally fed to the reaction column $RR_B$ at least as part of the feed stream $S_{BE1}$, these can be mixed beforehand and then fed as a feed stream $S_{AE1}$ or $S_{BE1}$ into the respective reaction column $RR_A$ or $RR_B$, or they are fed as separate streams into the respective reaction column $RR_A$ or $RR_B$.

4.6 Steps (e) and (h) of the Process According to the Invention

In step (e), energy, preferably heat, is transferred from a heating vapour $H_1$ having a pressure $p_1$ to at least one component $Q_1$, as a result of which the heating vapour $H_1$ condenses at least partially and a condensate $K_1$ is thus obtained.

In step (h), energy is transferred from a heating vapour $H_4$ having a pressure $p_4$ to at least one component $Q_2$, as a result of which, in particular, the heating vapour $H_4$ condenses at least partially and a condensate $K_2$ is thus obtained.

For the purposes of the invention, any vapour stream can be used as heating vapour $H_1$ or $H_4$. For the purposes of the invention, it can, for example, comprise n-butane or water. It is preferably steam.

"Component $Q_1$" and "component $Q_2$" are, according to the invention, collective terms for the mixtures and crude products $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$.

In other words, $Q_1$ is selected from the group consisting of $S_{AE1}$, $S_{AE2}$, $RP_A$, $S_{AS}$, $S_{AB}$, $G_A$, $S_{DAS}$, $S_{DAB}$, and can, when step (a2) is carried out, alternatively or additionally be selected from the group consisting of $S_{BE1}$, $S_{BE2}$, $RP_B$, $S_{BS}$, $S_{BB}$, and can also, when step (d) is carried out, alternatively or additionally be selected from the group consisting of $G_X$, $S_{XB}$, $S_{XS}$.

$Q_2$ can be selected correspondingly: $Q_2$ is selected from the group consisting of $S_{AE1}$, $S_{AE2}$, $RP_A$, $S_{AS}$, $S_{AB}$, $G_A$, $S_{DAS}$, $S_{DAB}$, and can, when step (a2) is carried out, alternatively or additionally be selected from the group consisting of $S_{BE1}$, $S_{BE2}$, $RP_B$, $S_{BS}$, $S_{BB}$, and can also, when step (d) is carried out, alternatively or additionally be selected from the group consisting of $G_X$, $S_{XB}$, $S_{XS}$.

This means that in the embodiments of the process of the invention in which the step (a2) is carried out but step (d) is not carried out, the component $Q_1$ is selected from $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, and in the embodiments of the process of the invention in which step (d) is carried out but step (a2) is not carried out, the component $Q_1$ is selected from $S_{AE1}$, $S_{AE2}$, $RP_A$, $S_{AS}$, $S_{AB}$, $G_A$, $S_{DAS}$, $S_{DAB}$, $G_X$, $S_{XB}$, $S_{XS}$, and in the embodiments of the process of the invention in which both steps (a2) and (d) are carried out, the component $Q_1$ is selected from $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$.

This means that in the embodiments of the process of the invention in which step (a2) is carried out but step (d) is not carried out, the component $Q_2$ is selected from $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, and in the embodiments of the process of the invention in which step (d) is carried out but step (a2) is not carried out, the component $Q_2$ is selected from $S_{AE1}$, $S_{AE2}$, $RP_A$, $S_{AS}$, $S_{AB}$, $G_A$, $S_{DAS}$, $S_{DAB}$, $G_X$, $S_{XB}$, $S_{XS}$, and in the embodiments of the process of the invention in which both steps (a2) and (d) are carried out, the component $Q_2$ is selected from $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$.

$Q_1$ and $Q_2$ are identical or different and are preferably identical.

When $Q_1$ and $Q_2$ are identical, this means, according to the invention, that the mixture or the stream selected from $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$ to which energy is transferred from heating vapour $H_1$ in step (e) is identical to the mixture or the stream selected from $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$ to which energy is transferred from heating vapour $H_4$ in step (h).

When $Q_1$ and $Q_2$ are different, this means, according to the invention, that the mixture or the stream selected from $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$ to which energy is transferred from heating vapour $H_1$ in step (e) is different from the mixture or the stream selected from $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$ to which energy is transferred from heating vapour $H_4$ in step (h).

In the embodiments of the present invention in which more than one column $RD_X$ is used for separating $S_{DAS}$, "$S_{XS}$" designates the group consisting of the bottom stream $S_{XS1}$ and the n bottom streams $S_{XS(n+1)}$, where "$S_{XS(n+1)}$" is the respective bottom stream from the rectification column $RD_{X(n+1)}$.

In the embodiments of the present invention in which more than one column $RD_X$ is used for separating $S_{DAS}$, "$S_{XB}$" designates the group consisting of the vapour stream $S_{XB1}$ and the n vapour streams $S_{XB(n+1)}$, where "$S_{XB(n+1)}$" is the respective vapour stream from the rectification column $RD_{X(n+1)}$.

In the embodiments of the present invention in which more than one column $RD_X$ is used for separating $S_{DAS}$, "$G_X$" designates the group consisting of the mixture $G_{X1}$ and the n mixtures $G_{X(n+1)}$, where "$G_{X(n+1)}$" is the respective mixture $G_X$ in the rectification column $RD_{X(n+1)}$.

The at least one component $Q_1$ is, in a preferred embodiment of the present invention, selected from the group consisting of $S_{AE1}$, $S_{AE2}$, $RP_A$, $S_{AS}$, $G_A$, $S_{DAS}$, where, when step (a2) is carried out, the at least one component $Q_1$ can alternatively or additionally be selected from $S_{BE1}$, $S_{BE2}$, $RP_B$, $S_{BS}$, and where, when step (d) is carried out, the at least one component $Q_1$ can alternatively or additionally be selected from $G_X$, $S_{XS}$.

In a more preferred embodiment of the present invention, the at least one component $Q_1$ is selected from the group consisting of $RP_A$, $S_{AS}$, $G_A$, $S_{DAS}$, where, when step (a2) is carried out, the at least one component $Q_1$ can alternatively or additionally be selected from $RP_B$, $S_{BS}$, and where, when step (d) is carried out, the at least one component $Q_1$ can alternatively or additionally be selected from $G_X$, $S_{XS}$.

In an even more preferred embodiment of the present invention, the at least one component $Q_1$ is selected from the group consisting of $G_A$, $S_{DAS}$, and where, when step (d) is carried out, the at least one component $Q_1$ can alternatively or additionally be selected from $G_X$, $S_{XS}$.

In an even more preferred embodiment of the present invention, the at least one component $Q_1$ is selected from the group consisting of $G_A$, $S_{DAS}$.

In a preferred embodiment of the present invention, the at least one component $Q_2$ is selected from the group consisting of $S_{AE1}$, $S_{AE2}$, $RP_A$, $S_{AS}$, $G_A$, $S_{DAS}$, where, when step (a2) is carried out, the at least one component $Q_2$ can alternatively or additionally be selected from $S_{BE1}$, $S_{BE2}$, $RP_B$, $S_{BS}$, and where, when step (d) is carried out, the at least one component $Q_2$ can alternatively or additionally be selected from $G_X$, $S_{XS}$.

In a more preferred embodiment of the present invention, the at least one component $Q_2$ is selected from the group consisting of $RP_A$, $S_{AS}$, $G_A$, $S_{DAS}$, where, when step (a2) is carried out, the at least one component $Q_2$ can alternatively or additionally be selected from $RP_B$, $S_{BS}$, and where, when step (d) is carried out, the at least one component $Q_2$ can alternatively or additionally be selected from $G_X$, $S_{XS}$.

In a further preferred embodiment of the present invention, the at least one component $Q_2$ is selected from the group consisting of $G_A$, $S_{DAS}$, and where, when step (d) is carried out, the at least one component $Q_2$ can alternatively or additionally be selected from $G_X$, $S_{XS}$.

In an even more preferred embodiment of the present invention, the at least one component $Q_2$ is selected from group consisting of $G_A$, $S_{DAS}$.

The energy of the heating vapour $H_1$ or $H_4$ can be transferred to the at least one component $Q_1$ or $Q_2$ in step (e) or step (h) of the process of the invention by methods known to those skilled in the art. In particular, a heat exchanger WT is used for this purpose. All heat exchangers which are well known to a person skilled in the art for this purpose can be utilized as heat exchanger WT (also referred to as "heat exchanger"). This is preferably a vaporizer, more preferably selected from bottom vaporizer VS, intermediate vaporizer VZ.

The transfer of energy from the heating vapour $H_1$ or $H_4$ to the at least one component $Q_1$ or $Q_2$ is, according to the invention, effected in particular by heat being transferred from the heating vapour $H_1$ or $H_4$ to the at least one component $Q_1$ or $Q_2$, so that the heating vapour $H_1$ or $H_4$ heats the at least one component $Q_1$ or $Q_2$.

The transfer of energy from the heating vapour $H_1$ to the at least one component $Q_1$ occurs in particular, directly or indirectly.

The transfer of energy from the heating vapour $H_4$ to the at least one component $Q_2$ occurs, in particular, directly or indirectly.

In the case of $H_1$ and $Q_1$, "directly" means that $H_1$ is contacted with the at least one component $Q_1$ so that energy, preferably heat, is transferred from $H_1$ to the at least one component $Q_1$. Contacting here preferably takes place in a heat exchanger WT, even more preferably in a vaporizer.

In the case of $H_4$ and $Q_2$, "directly" means that $H_4$ is contacted with the at least one component $Q_2$, so that energy, preferably heat, is transferred from $H_4$ to the at least one component $Q_2$. The contacting here preferably takes place in a heat exchanger WT, even more preferably in a vaporizer.

It goes without saying that both in the case of "direct" and in the case of "indirect" energy transfer, $H_1$ and $Q_1$ or $H_4$ and $Q_2$ or $H_1$ or $H_4$ and $W_1$ do not mix since no condensate $K_1$ or $K_2$ would then be obtained. The contacting without mixing is achieved by methods known to those skilled in the art, for example by contacting via a dividing wall composed of metal, polymer, etc., in particular in the heat exchanger WT.

In the case where $Q_1$ or $Q_2$ is $S_{AE1}$, the direct energy transfer from $H_1$ or $H_4$ to $S_{AE1}$ is carried out, in particular, by $S_{AE1}$ and $H_1$ or $H_4$ being conveyed through a heat exchanger WT (e.g. <WA4> in FIGS. 1 to 4) before $S_{AE1}$ is introduced into the reaction column $RR_A$, so that $S_{AE1}$ contacts the heating vapour $H_1$ or the heating vapour $H_4$ in the heat exchanger WT and energy is thus transferred from $H_1$ or $H_4$ to $S_{AE1}$.

In the case where $Q_1$ or $Q_2$ is $S_{AE2}$, the direct energy transfer from $H_1$ or $H_4$ to $S_{AE2}$ is, in particular, carried out by $S_{AE2}$ and $H_1$ or $H_4$ being conveyed through a heat exchanger WT (e.g. <WA5> in FIGS. 1 to 4) before $S_{AE2}$ is introduced into the reaction column $RR_A$, so that $S_{AE2}$ contacts the heating vapour $H_1$ or the heating vapour $H_4$ in the heat exchanger WT and energy is thus transferred from $H_1$ or $H_4$ to $S_{AE2}$.

In the case where $Q_1$ or $Q_2$ is $RP_A$, the direct energy transfer from $H_1$ or $H_4$ to $RP_A$ is, in particular, carried out by $RP_A$ being discharged as stream $S_{RRAZ}$ from the column $RR_A$ and $S_{RRAZ}$ and $H_1$ or $H_4$ being conveyed through a heat exchanger WT, preferably an intermediate vaporizer $VZ_{RRA}$ (e.g. <WA3> in FIGS. 1 to 4) on the reaction column $RR_A$, so that $S_{RRAZ}$ contacts the heating vapour $H_1$ or the heating vapour $H_4$ in the heat exchanger WT and energy is thus transferred from $H_1$ or $H_4$ to $S_{RRAZ}$. $S_{RRAZ}$ is then recirculated to the other $RP_A$ in $RR_A$.

In the case where $Q_1$ or $Q_2$ is $S_{AS}$, the direct energy transfer from $H_1$ or $H_4$ to $S_{AS}$ is, in particular, carried out by $S_{AS}$ and $H_1$ or $H_4$ being conveyed through a heat exchanger WT, preferably a bottom vaporizer $VS_{RRA}$ (e.g. <WA1> in FIGS. 1 to 4) on the reaction column $RR_A$, so that $S_{AS}$ contacts the heating vapour $H_1$ or the heating vapour $H_4$ in the heat exchanger WT and energy is thus transferred from $H_1$ or $H_4$ to $S_{AS}$.

In the case where $Q_1$ or $Q_2$ is $S_{AB}$, the direct energy transfer from $H_1$ or $H_4$ to $S_{AB}$ is, in particular, carried out by $S_{AB}$ and $H_1$ or $H_4$ being conveyed through a heat exchanger WT (e.g. <WA6> in FIGS. 1 to 4), so that $S_{AB}$ contacts the heating vapour $H_1$ or the heating vapour $H_4$ in the heat exchanger WT and energy is thus transferred from $H_1$ or $H_4$ to $S_{AB}$.

In the case where $Q_1$ or $Q_2$ is $G_A$, the direct energy transfer from $H_1$ or $H_4$ to $G_A$ is, in particular, carried out by $G_A$ being discharged as stream $S_{AZ}$ from the column $RR_A$ and $S_{AZ}$ and $H_1$ or $H_4$ being conveyed through a heat exchanger WT, preferably an intermediate vaporizer $VZ_A$ (e.g. <W9> in FIGS. 1 to 4) on the rectification column $RD_A$, so that $S_{AZ}$ contacts the heating vapour $H_1$ or the heating vapour $H_4$ in the heat exchanger WT and energy is thus transferred from $H_1$ or $H_4$ to $S_{AZ}$. $S_{AZ}$ is then recirculated to the other $G_A$ in $RD_A$.

In the case where $Q_1$ or $Q_2$ is $S_{DAS}$, the direct energy transfer from $H_1$ or $H_4$ to $S_DAS$ is, in particular, carried out by $S_{DAS}$ and $H_1$ or $H_4$ being conveyed through a heat exchanger WT, preferably a bottom vaporizer $VS_A$ (e.g. <W7> in FIGS. 1 to 4) to the rectification column $RD_A$, so that $S_DAS$ contacts the heating vapour $H_1$ or the heating vapour $H_4$ in the heat exchanger WT and energy is thus transferred from $H_1$ or $H_4$ to $S_{DAS}$.

In the case where $Q_1$ or $Q_2$ is $S_{DAB}$, the direct energy transfer from $H_1$ or $H_4$ to $S_{DAB}$ is, in particular, carried out by $S_{DA}B$ and $H_1$ or $H_4$ being conveyed through a heat exchanger WT (not shown in the figures), so that $S_{DAB}$ contacts the heating vapour $H_1$ or the heating vapour $H_4$ in the heat exchanger WT and energy is thus transferred from $H_1$ or $H_4$ to $S_{DAB}$.

In the case where $Q_1$ or $Q_2$ is $S_{BE1}$, the direct energy transfer from $H_1$ or $H_4$ to $S_{BE1}$ is, in particular, carried out by $S_{BE1}$ and $H_1$ or $H_4$ being conveyed through a heat exchanger WT (e.g. <WB4> in FIG. 4) before $S_{BE1}$ is introduced into the reaction column $RR_B$, so that $S_{BE1}$ contacts the heating vapour $H_1$ or the heating vapour $H_4$ in the heat exchanger WT and energy is thus transferred from $H_1$ or $H_4$ to $S_{BE1}$.

In the case where $Q_1$ or $Q_2$ is $S_{BE2}$, the direct energy transfer from $H_1$ or $H_4$ to $S_{BE2}$ is, in particular, carried out by $S_{BE2}$ and $H_1$ or $H_4$ being conveyed through a heat exchanger WT (e.g. <WBA5> in FIG. 4) before $S_{BE2}$ is introduced into the reaction column $RR_B$, so that $S_{BE2}$ contacts the heating vapour $H_1$ or the heating vapour $H_4$ in the heat exchanger WT and energy is thus transferred from $H_1$ or $H_4$ to $S_{BE2}$.

In the case where $Q_1$ or $Q_2$ is $RP_B$, the direct energy transfer from $H_1$ or $H_4$ to $RP_B$ is, in particular, carried out by $RP_B$ being discharged as stream $S_{RRBZ}$ from the column $RR_B$ and $S_{RRBZ}$ and $H_1$ or $H_4$ being conveyed through a heat exchanger WT, preferably an intermediate vaporizer $VZ_{RRB}$ (e.g. <WB3> in FIG. 4) on the reaction column $RR_B$, so that $S_{RRBZ}$ contacts the heating vapour $H_1$ or the heating vapour $H_4$ in the heat exchanger WT and energy is thus transferred from $H_1$ or $H_4$ to $S_{RRBZ}$. $S_{RRBZ}$ is then recirculated to the other $RP_B$ in $RR_B$.

In the case where $Q_1$ or $Q_2$ is $S_{BS}$, the direct energy transfer from $H_1$ or $H_4$ to $S_{BS}$ is, in particular, carried out by $S_B S$ and $H_1$ or $H_4$ being conveyed through a heat exchanger WT, preferably a bottom vaporizer $VS_{RRB}$ (e.g. <WB1> in FIG. 4) on the reaction column $RR_B$, so that $S_{BS}$ contacts the heating vapour $H_1$ or the heating vapour $H_4$ in the heat exchanger WT and energy is thus transferred from $H_1$ or $H_4$ to $S_{BS}$.

In the case where $Q_1$ or $Q_2$ is $S_{BB}$, the direct energy transfer from $H_1$ or $H_4$ to $S_{BB}$ is, in particular, carried out by $S_{BB}$ and $H_1$ or $H_4$ being conveyed through a heat exchanger WT (e.g. <WB6> in FIG. 4), so that $S_{BB}$ contacts the heating vapour $H_1$ or the heating vapour $H_4$ in the heat exchanger WT and energy is thus transferred from $H_1$ or $H_4$ to $S_{BB}$.

In the case where $Q_1$ or $Q_2$ is $G_X$, the direct energy transfer from $H_1$ or $H_4$ to $G_X$ is, in particular, carried out by $G_X$ being discharged as stream $S_{XZ}$ from the column $RD_X$ and $S_{XZ}$ and $H_1$ or $H_4$ being conveyed through a heat exchanger WT, preferably an intermediate vaporizer $VZ_X$ (e.g. <W13> in FIG. 4) on the rectification column $RD_X$, so that $S_{XZ}$ contacts the heating vapour $H_1$ or the heating vapour $H_4$ in the heat exchanger WT and energy is thus transferred from $H_1$ or $H_4$ to $S_{XZ}$. $S_{XZ}$ is then recirculated to the other $G_X$ in $RD_X$.

In the case where $Q_1$ or $Q_2$ is $S_{XS}$, the direct energy transfer from $H_1$ or $H_4$ to $S_{XS}$ is, in particular, characterized by $S_{XS}$ and $H_1$ or $H_4$ being conveyed through a heat exchanger WT, preferably a bottom vaporizer $VS_X$ (e.g. <W11> in FIG. 4) on the rectification column $RD_X$, so that $S_{XS}$ contacts the heating vapour $H_1$ or the heating vapour $H_4$ in the heat exchanger WT and energy is thus transferred from $H_1$ or $H_4$ to $S_{XS}$.

In the case where $Q_1$ or $Q_2$ is $S_{XB}$, the direct energy transfer from $H_1$ or $H_4$ to $S_{XB}$ is, in particular, characterized by $S_{XB}$ and $H_1$ or $H_4$ being conveyed through a heat exchanger WT (not shown in the figures), so that $S_{XB}$ contacts the heating vapour $H_1$ or the heating vapour $H_4$ in the heat exchanger WT and energy is thus transferred from $H_1$ or $H_4$ to $S_{XB}$.

In the case of $H_1$ and $Q_1$, "indirect" means that energy is transferred from heating vapour $H_1$ to a heat transfer medium $W_1$, in particular $H_1$ is contacted with a heat transfer medium $W_1$, so that energy, preferably heat, is transferred from $H_1$ to $W_1$ and the energy of $W_1$ is subsequently transferred to the at least one component $Q_1$. The transfer of the energy from $W_1$ to $Q_1$ can in turn take place directly or indirectly, i.e. by $W_1$ being contacted with the at least one component $Q_1$, so that energy, preferably heat, of $W_1$ goes over ("directly") to the at least one component $Q_1$ or so that the energy of $W_1$ is firstly transferred to one or more further heat transfer media $W_2$, $W_3$, $W_4$ etc., and the last of these heat exchangers, designated as "$W_Y$" is contacted with the at least one component $Q_1$, so that energy, preferably heat, goes over from $W_Y$ to the at least one component $Q_1$. The contacting described preferably takes place in each case in a heat exchanger WT, even more preferably in a vaporizer.

In the case of indirect energy transfer from $H_1$ to the at least one component $Q_1$, preference is given to $H_1$ being contacted with a heat transfer medium $W_1$ so that energy, preferably heat, goes over from $H_1$ to $W_1$ and the energy of $W_1$ is subsequently transferred to $Q_1$ by contacting of $W_1$ with the at least one component $Q_1$ in a heat exchanger WT.

The transfer of energy from $W_1$ to $Q_1$ can, in the embodiment in which $W_1$ is a stream comprising essentially water and/or the alcohol ROH, also be carried out by $W_1$ being mixed with the at least one component $Q_1$ after energy has been transferred from heating vapour $H_1$ to $W_1$, preferably in a heat exchanger WT. This embodiment is particularly advantageous when the at least one component $Q_1$ is selected from the group consisting of $RP_A$, $G_A$, $RP_B$, $G_X$, preferably from $G_A$, $G_X$.

"Stream comprising essentially water and/or alcohol ROH" means, in particular, that the proportion by mass of alcohol ROH and water in the stream is ≥90% by weight, preferably ≥96% by weight or ≥99% by weight. Even more preferably, it means that the ratio of the mass of water comprised by the stream to alcohol ROH comprised by the stream is less than 1:1, preferably 1:5, more preferably 1:9, more preferably 1:49, even more preferably 1:99, even more preferably 1:999.

In the case of $H_4$ and $Q_2$, "indirect" means that energy is transferred from heating vapour $H_4$ to a heat transfer medium $W_1$, in particular $H_4$ is contacted with a heat transfer medium $W_1$, so that energy, preferably heat, is transferred from $H_4$ to $W_1$ and the energy of $W_1$ is subsequently transferred to the at least one component $Q_2$. The transfer of energy from $W_1$ to $Q_2$ can in turn take place directly or indirectly, i.e. by $W_1$ being contacted with the at least one component $Q_2$ so that energy, preferably heat, goes over ("directly") from $W_1$ to the at least one component $Q_2$ or so that the energy of $W_1$ is firstly transferred to one or more further heat transfer media $W_2$, $W_3$, $W_4$ etc., and the last of these heat transfer media, designated as "$W_Y$" is contacted with the at least one component $Q_2$ so that energy, preferably heat, goes over from $W_Y$ to the at least one component $Q_2$. The contacting events described in each case preferably take place in a heat exchanger, even more preferably in a vaporizer.

In the case of indirect energy transfer from $H_4$ to the at least one component $Q_2$, preference is given to $H_4$ being contacted with a heat transfer medium $W_1$, so that energy, preferably heat, goes over from $H_4$ to $W_1$ and the energy of $W_1$ is subsequently transferred to $Q_2$ by contacting of $W_1$ with the at least one component $Q_2$ in a heat exchanger WT.

In the embodiment in which $W_1$ is a stream comprising essentially water and/or the alcohol ROH, the indirect transfer of energy from $W_1$ to the at least one component $Q_2$ is preferably carried out so that $W_1$ is mixed with the at least one component $Q_2$ after energy has been transferred from the heating vapour $H_1$ to $W_1$, preferably in a heat exchanger WT. This embodiment is particularly advantageous when the at least one component $Q_2$ is selected from the group consisting of $RP_A$, $G_A$, $RP_B$, $G_X$, preferably from $G_A$, $G_X$.

The mixing of $W_1$ with the at least one component $Q_1$ or the at least one component $Q_2$ is, in particular, carried out by $W_1$, for example when the component $Q_1$ or $Q_2$ is a stream $S_{AE1}$, $S_{AE2}$, $S_{AS}$, $S_{AB}$, $S_{DAS}$, $S_{DAB}$, $S_{BE1}$, $S_{BE2}$, $S_{BS}$, $S_{BB}$, $S_{XB}$, $S_{XS}$, being introduced into the respective stream in the conduit. When the component $Q_1$ or $Q_2$ is one of the mixtures $RP_A$, $G_A$, $RP_B$, $G_X$, $W_1$ can advantageously be introduced into the column in which the mixture concerned is present, thus in the case of $RP_A$ in $RR_A$, in the case of $RP_B$ in $RR_B$, in the case of $G_A$ in $RD_A$ and in the case of $G_X$ in $RD_X$.

According to the invention, $W_1$ and all heat transfer media $W_2$, $W_3$, $W_4$ etc., which may be used in indirect energy transfer are none of $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$.

This also encompasses, according to the invention, the case where $W_1$, $W_2$, $W_3$, $W_4$ etc., comprises the same material as one of $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$ and differs only from the stream or the mixture in terms of the proportion by mass of the material.

Any heat transfer medium known to those skilled in the art can be utilized as heat transfer medium $W_1$ and optionally further heat transfer media $W_2$, $W_3$, $W_4$ etc., employed. The heat transfer media are preferably selected from the group consisting of water; alcohols, preferably the alcohol ROH; alcohol-water solutions, preferably ROH-water solutions; salt-water solutions, including ionic liquids such as LiBr solutions, dialkylimidazolium salts such as, in particular, dialkylimidazolium dialkylphosphates; mineral oils such as diesel oils; heat transfer oils such as silicone oils, biological oils such as limonene; aromatic hydrocarbons such as dibenzyl toluene. The greatest preference is given to using water, alcohol or alcohol-water solutions as heat transfer medium, in particular as heat transfer medium $W_1$, where the alcohol is preferably the alcohol ROH and the alcohol is the same alcohol as is also used in step (a1) and optionally in step (a2).

Salt-water solutions that may be used are also described for example in DE 10 2005 028 451 A1 and WO 2006/134015 A1.

This embodiment in which energy is transferred indirectly is accordingly particularly advantageous when fresh alcohol ROH is to be introduced into the system.

In the context of the invention, "bar" always means "bar absolute" (="bar abs.").

$H_1$ has, in particular, a temperature $T_1$ of from 101° C. to 270° C., preferably from 105° C. to 250° C., preferably from 130° C. to 200° C. $H_1$ preferably has a pressure of from 1 to 55 bar, more preferably from 2 to 5 bar, even more preferably 4 bar. As heating vapour $H_1$, it is also possible to use a vapour having a pressure of >30 bar.

The heating vapour $H_1$ condenses at least partially on transfer of the energy, as a result of which a condensate $K_1$ is obtained at a pressure of from 1 to 55 bar, preferably from 2 to 5 bar, particularly preferably 4 bar, and a temperature of from 101° C. to 270° C., preferably from 105° C. to 250° C., more preferably from 110° C. to 200° C.

The heating vapour condensate $K_1$ is preferably collected in a condensate vessel. All vessels known to those skilled in the art, e.g. steel vessels, can be utilized for the purpose.

4.7 Step (f) of the Process According to the Invention

In step (f) of the process according to the invention, $K_1$ is at least partially depressurized to give a heating vapour $H_2$ having a pressure $p_2$ and a temperature $T_2$, where $p_2 < p_1$.

The depressurization of the heating vapour condensate $K_1$ is preferably carried out by introducing $K_1$ into a condensate vessel in which the hot condensate can be separated from the vapour. In a preferred embodiment of the process of the invention, $K_1$ is utilized for heating streams and/or mixtures in the process before it is depressurized to give a heating vapour $H_2$. Likewise, the remaining condensate which remains in the liquid state after depressurization to $p_2$ can be utilized for heating streams and/or mixtures in the process.

The pressure in the condensate vessel is preferably lower than in the heat exchanger (in which $H_1$ is condensed at least partially) on the heating vapour side. Owing to the lower pressure, part of the hot condensate $K_1$ can vaporize, as a result of which the entire vapour, i.e. the uncondensed part of the heating vapour and the hot condensate which has been vaporized by depressurization in the condensate vessel is obtained as heating vapour $H_2$ in the condensate vessel. This heating vapour $H_2$ is, in particular, low-pressure vapour and preferably has a pressure $p_2$ which is such that the ratio $p_2/p_1$ (bar/bar) is in the range from 0.001 to 0.999, preferably from 0.01 to 0.9, more preferably from 0.05 to 0.8, more preferably from 0.1 to 0.7, more preferably from 0.15 to 0.6, more preferably from 0.2 to 0.5.

In another preferred embodiment, the temperature $T_2$ of $H_2$ is below the temperature $T_1$ of $H_1$. It is then preferred that $T_2$ is >0° C., and the ratio of temperature $T_2/T_1$ (° C./° C.) is in the range from 0.1 to 0.999, more preferably from 0.2 to 0.995, more preferably from 0.3 to 0.990.

The condensate $K_1$ can be composed of not only the condensate obtained from the condensation of $H_1$ but also further heating vapour condensates, for instance when various heating vapours are used in the process of the invention and energy is thus transferred to various components $Q_1$ from different heating vapours. In this embodiment, a plurality of condensates $K_1$ are then obtained and these can be combined and depressurized in step (f) to give heating vapour $H_2$.

Such a preferred embodiment is shown, for example, in FIG. 3. The condensate $K_1$ collected in the condensate vessel <86> is a mixture of the condensates <71> and <81> and additionally <88>. The condensate <81> is obtained from the condensation of the heating vapour <84> on transfer of energy to $G_A$ in the intermediate vaporizer $VZ_A$<W9>. The condensate <71> is obtained from the condensation of the heating vapour <74> on transfer of energy to $G_A$ in the bottom vaporizer $VS_A$<W8>.

The hot condensates from these two vaporizers are then conveyed according to the above statements to a condensate vessel <86>. The heating vapour $H_2$<82> obtained there is then used in the regulatable vapour ejector <89>, the mixed vapour from which is reused as new heating vapour $H_4$<84> in the intermediate vaporizer $VZ_A$<W9>. The advantage of this variant is that the hot condensate obtained can be depressurized further in order to be able to provide a greater amount of low-pressure vapour.

FIG. 4 shows a corresponding routing of the condensate and heating vapour streams on the rectification column $RD_X<3>$.

4.8 Step (a) of the Process According to the Invention

In step (g) of the process of the invention, $H_2$ is mixed with further heating vapour $H_3$ having a pressure $p_3$ and a temperature $T_3$ so as to give a mixed heating vapour $H_4$ having a pressure $p_4$ and a temperature $T_4$, where $p_2<p_4<p_3$ and in particular $p_1<p_3$.

The condensate $K_1$ and thus the heating vapour $H_2$ still contains energy which is not exploited in any known process for producing alkali metal alkoxides. However, this is not sensible from an energy and economic point of view. This energy can be utilized in the process of the present invention.

The mixing of $H_2$ with further heating vapour $H_3$ can be carried out by any method known to those skilled in the art, in particular by combining the two heating vapours by means of a Venturi nozzle.

In a preferred embodiment of the process of the invention, the vapour $H_2$ is mixed with further vapour having a pressure $p<p_3$ and the vapour obtained then is mixed with $H_3$.

The mixing of $H_2$ with further heating vapour $H_3$ is preferably carried out by means of a, preferably regulatable, vapour ejector DS (thermocompressor). The thermocompressor is then supplied both with further heating vapour $H_3$, which originates from an appropriate vapour network, and also with the low-pressure vapour $H_2$ from the condensate vessel, forming a mixed vapour $H_4$ which is accordingly the heat transfer medium. The mixed vapour in this embodiment is accordingly the heating vapour $H_4$.

Such a vapour ejector DS is shown in FIG. 5. It is configured so that it is operated using a driving vapour having a relatively high pressure and can draw in a suction vapour having a lower pressure, as a result of which a mixed vapour which is used as heat transfer medium is formed. The driving vapour is in the present case the heating vapour or the driving vapour $H_3$ by means of which the heating vapour $H_2$ is drawn as suction vapour from the condensate vessel and mixed with the driving vapour $H_3$.

The advantage of such a configuration is obvious. Part of the energy of the low-pressure vapour obtained in the condensate vessel can be utilized and energy and costs can thus be saved. Such a procedure can also be advantageous for another reason. The vapour ejector used can be regulatable so that the amounts of intermediate-pressure vapour $H_3$ and low-pressure vapour $H_2$ can be adjusted, for example as a function of particular process parameters. The amount of suction vapour is established via the amount of driving vapour. The amount of intermediate-pressure vapour $H_3$ and low-pressure vapour $H_2$ can, for example, be set as a function of the temperature of the at least one component $Q_1$.

The pressure $p_3$ of the heating vapour $H_3$ is greater than $p_2$ and can otherwise be selected in a wide range. The invention is suitable for situations in which heating vapour $H_3$ on whose pressure and temperature little influence can be exerted and which then has to be set to a given value $H_4$ arises. Thus, $p_2<p_4<p_3$.

In a particular embodiment of the process of the invention, $p_2<p_1<p_3$, especially when $Q_1$ and $Q_2$ are identical.

The heating vapour $H_3$ used preferably has a pressure $p_3$ in the range from 2 bar to 80 bar and preferably has a temperature $T_3$ of from 120° C. to 300° C., where at the same time $p_4<p_3$ and preferably also $p_1<p_3$.

4.9 Step (h) of the Process According to the Invention

In step (h), energy is transferred from heating vapour $H_4$ having a pressure $p_4$ and a temperature $T_4$ to at least one component $Q_2$.

The meaning of the component $Q_2$ is defined above in the context of step (e), section 4.6.

In a preferred embodiment of the present invention, the heating vapour $H_4$ condenses at least partially and a condensate $K_2$ is thus obtained.

$H_4$ has, in particular, a temperature $T_4$ of from 101° C. to 270° C., preferably from 105° C. to 250° C., more preferably from 110° C. to 200° C. $H_4$ preferably has a pressure of from 1 to 55 bar, preferably from 2 to 5 bar, more preferably 4 bar. As heating vapour $H_4$, it is also possible to use a vapour having a pressure of >30 bar.

The heating vapour $H_4$ condenses at least partially, in particular, on transfer of the energy, as a result of which a condensate $K_2$ is preferably obtained at a pressure of from 1 to 55 bar, preferably from 2 to 5 bar, particularly preferably 4 bar, and a temperature of from 101° C. to 270° C., preferably from 105° C. to 250° C., more preferably from 110° C. to 200° C.

The heating vapour condensate $K_2$ is preferably collected in a condensate vessel. For this purpose, it is possible to utilize all condensate vessels known to those skilled in the art, e.g. vessels made of steel.

The advantage of the present invention is, inter alia, that the sequence of steps (f), (g), (h) can be carried out in a cycle and the condensate $K_2$ obtained after step (h) by the at least partial condensation of $H_4$ is reused as condensate $K_1$ in a new cycle of step (f), (g), (h).

This is advantageous especially when $Q_1$ and $Q_2$ are identical.

In a preferred embodiment of the present invention, the heating vapour $H_4$ is therefore at least partially condensed so as to give a condensate $K_2$ by means of which a further step (f) in which the condensate $K_2$ is then used as condensate $K_1$ is carried out after step (h).

This allows the process of the invention to be carried out continuously and the heating of the corresponding components $Q_1$ and $Q_2$ to be carried out in the circuit.

In the process of the invention, $p_1$ and $p_4$, are preferably similar, i.e. the ratio of $p_1/p_4$ is preferably in the range from 0.5 to 1.5, more preferably from 0.8 to 1.2, more preferably from 0.9 to 1.1, even more preferably from 0.99 to 1.01, most preferably 1.

5. EXAMPLES

5.1 Example (not According to the Invention)

Comparative Example 1 is carried out in an apparatus corresponding to FIG. 1.

A stream of aqueous NaOH $S_{AE2}<1A2>$ (48.5% by weight of NaOH, 51.5% by weight of water) of 459 kg/h is fed in at room temperature at the top of a reaction column $RR_A<1A>$ having a pressure at the top of 1.6 bar abs.

A methanol stream $S_{AE1}<1A1>$ in vapour form having a low level of contamination with water is introduced in countercurrent at a rate of 6962 kg/h at the bottom of the reaction column $<1A>$.

A methanol/water mixture $S_{AB}$<1A5> is obtained at the top of the reaction column and of this 551 kg/h are condensed by means of a condenser and recirculated to the column <1A> (not shown in the figures) and 6421 kg/h are conveyed further via a compressor $VD_{31}$<11> to the column $RD_A$<2>.

At the bottom of the column $RR_A$<1A>, a virtually water-free product stream $S_{AS}$<1A4> is discharged from the column. Of this, 1000 kg/h are discharged as product stream from the process. The other part is fed to the bottom vaporizer $V_{SRRA}$<WA1>. 294 kg/h of heating vapour (11 bar abs., 190° C.) are depressurized through a regulating valve <85> to 4 bar abs. and energy is thus transferred to this part of the stream $S_{AS}$<1A4> taken off via the bottom vaporizer $VS_{RRA}$<WA1>, resulting in the heating vapour condensing and the product stream $S_{AS}$<1A4> taken off partially vaporizing and the desired MeOH content thus being established in the bottom product $S_{AS}$<1A4>. The uncondensed part of the overhead stream $S_{AB}$<1A5> (6421 kg/h of MeOH/water mixture) is conveyed via the compressor $VD_{31}$<11> (exit pressure 2.25 bar abs.) into the rectification column $RD_A$<2> (pressure at the top of column $RD_A$<2>=2.2 bar abs.).

At the top of the rectification column $RD_A$<2>, a methanol/water mixture $S_{DAB}$<24> which is enriched in methanol compared to the feed stream from the compressor $VD_{31}$<11> is obtained, and 878 kg/h of fresh methanol <25> are additionally fed to the column $RD_A$<2> at the top of the column.

At the bottom of the rectification column $RD_A$<2>, a stream $S_{DAS}$<22> which is enriched in water compared to the column feed from the compressor is obtained. Part of this stream is recirculated via the bottom vaporizer $VS_A$<W8> to the column <2>, with the remaining 337 kg/h being discharged as bottom product stream.

For operation of the bottom vaporizer $VS_A$<W8>, 3256 kg/h of heating vapour (11 bar abs., 190° C.) are depressurized through a regulating valve <85> to 4 bar abs. and energy is transferred to the recirculated stream via the bottom vaporizer $VS_A$<W8>, resulting in the heating vapour condensing.

The heating vapour condensate streams from <WA1> and <W8> are combined in a condensate vessel <86>. For recirculation into the condensate network, the condensate stream <87> exiting at about 143° C. is cooled to 75° C. by means of return cooling water. Here, about 285 kW are transferred to the return cooling water.

5.2 Example 2 (According to the Invention)

Example 2 is carried out in an apparatus corresponding to FIG. 2.

This example is a repetition of Example 1 with the following differences:

The collected condensate in the condensate vessel <86> is depressurized to 1.5 bar abs. This results in vaporization of about 217 kg/h of condensate <82>. The heating vapour <83> is not depressurized through a regulating valve <85> but instead is used as driving vapour for a regulatable vapour ejector <89> in order to draw in the stream <82> and mix it with <83>. The heating vapour <84> having a pressure of 4 bar abs. is obtained at the exit of <89>. As a result of the additional heating vapour from the depressurization of the condensate being utilized, only 3048 kg/h of fresh heating vapour <83> are acquired for operation of the bottom vaporizer $VS_A$<W8>.

A stream <84> (about 3265 kg/h) is obtained and this condenses as condensate <81> during operation of the bottom vaporizer $V_{SA}$<W8>. The resulting condensate stream <81> is then fed back into the condensate vessel <86>.

The condensate stream <87> is obtained at a temperature of only about 111° C. Thus, less return cooling water than in Example 1 is required for cooling to 75° C. and only about 142 kW are transferred to the cooling medium, i.e. only 50% of the amount required in Example 1.

In total, only 3342 kg/h of heating vapour (11 bar abs, 190° C.) are required as heating vapour for <WA1> and <WA8> in the procedure according to Example 2. Thus, about 6% of the 11 bar abs. heating vapour can be saved compared to Example 1.

The invention claimed is:

1. A process for producing at least one alkali metal alkoxide of the formula $M_AOR$, wherein R is a $C_1$-$C_6$ hydrocarbon radical and $M_A$ is sodium or potassium, comprising:

(a1) reacting a feed stream $S_{AE1}$ comprising ROH with a feed stream $S_{AE2}$ comprising $M_AOH$ in countercurrent in a reactive rectification column $RR_A$ to give a crude product mixture $RP_A$ comprising $M_AOR$, water, ROH, and $M_AOH$,
 wherein a bottom product stream $S_{AS}$ comprising ROH and $M_AOR$ is taken off at the lower end of $RR_A$ and a vapour stream $S_{AB}$ comprising water and ROH is taken off at the upper end of $RR_A$, (a2) optionally, simultaneously with, and spatially separately from step (a1), a feed stream $S_{BE1}$ comprising ROH is reacted with a feed stream $S_{BE2}$ comprising $M_BOH$ in countercurrent in a reactive rectification column $RR_B$ to give a crude product mixture $RP_B$ comprising $M_BOR$, water, ROH, $M_BOH$, where $M_B$ is selected from sodium or potassium,
 wherein a bottom product stream $S_{BS}$ comprising ROH and $M_BOR$ is taken off at the lower end of $RR_B$ and a vapour stream $S_{BB}$ comprising water and ROH is taken off at the upper end of $RR_B$, (b) the vapour stream $S_{AB}$, and, when step (a2) is carried out, the vapour stream $S_{BB}$, is/are mixed with $S_{AB}$ or, separately from $S_{AB}$, fed into a rectification column $RD_A$ so that a mixture $G_A$ comprising water and ROH is present in $RD_A$, (c) $G_A$ is separated in $RD_A$ into a vapour stream $S_{DAB}$ comprising ROH at the upper end of $RD_A$ and a bottom stream $S_{DAS}$ comprising water and ROH at the lower end of $RD_A$,
 wherein the bottom stream $S_{DAS}$ is discharged from $RD_A$ at an offtake point $E_{AS}$ at the lower end of $RD_A$ and the vapour stream $S_{DAB}$ is discharged from $RD_A$ at an offtake point $E_{AK}$ at the upper end of $RD_A$, (d) optionally, $S_{DAS}$ is, in its entirety or partly, separated in at least one rectification column $RD_X$ which is different from $RD_A$, and in which a mixture $G_X$ comprising water and ROH is present, into a vapour stream $S_{XB}$ comprising ROH at the upper end of $RD_X$ and a bottom stream $S_{XS}$ comprising water and optionally ROH at the lower end of $RD_X$,
 wherein the bottom stream $S_{XS}$ is discharged from the at least one rectification column $RD_X$ at an offtake point $E_{XS}$ at the lower end of this column and the vapour stream $S_{XB}$ is discharged from the at least one rectification column $RD_X$ at an offtake point $E_{XK}$ at the upper end of this column, (e) energy is transferred from a heating vapour $H_1$ having a pressure $p_1$ to at least one component $Q_1$, as a result of which the heating vapour $H_1$ condenses at least partially and a condensate $K_1$ is thus obtained, wherein:

(f) $K_1$ is at least partially depressurized to give a heating vapour $H_2$ having a pressure $p_2$, where $p_2 < p_1$, (g) $H_2$ is mixed with further heating vapour $H_3$ having a pressure $p_3$ so as to give a heating vapour $H_4$ having a pressure $p_4$, where $p_2 < p_4 < p_3$, (h) energy is transferred from $H_4$ to at least one component $Q_2$, wherein:

i) $Q_1$ and $Q_2$ are identical or different from one another, ii) $Q_1$ and $Q_2$ are selected from the group consisting of $S_{AE1}$, $S_{AE2}$, $RP_A$, $S_{AS}$, $S_{AB}$, $G_A$, $S_{DAS}$, $S_{DAB}$, iii) $Q_1$ and $Q_2$ can, when step (a2) is carried out, alternatively or additionally be selected from the group consisting of $S_{BE1}$, $S_{BE2}$, $RP_B$, $S_{BS}$, $S_{BB}$, iv) $Q_1$ and $Q_2$ can, when step (d) is carried out, alternatively or additionally be selected from the group consisting of $G_X$, $S_{XB}$, $S_{XS}$.

2. The process of claim 1, wherein the heating vapour $H_1$ is contacted with the at least one component $Q_1$ so that energy is transferred from $H_1$ to the at least one component $Q_1$ and the heating vapour $H_4$ is contacted with the at least one component $Q_2$ so that energy is transferred from $H_4$ to the at least one component $Q_2$.

3. The process of claim 1, wherein energy is transferred from heating vapour $H_1$ to a heat transfer medium $W_1$ and the energy of $W_1$ is subsequently transferred to the at least one component $Q_1$ and energy from heating vapour $H_4$ is transferred to $W_1$ and energy is subsequently transferred from $W_1$ to the at least one component $Q_2$, where $W_1$ is none of $S_{AE1}$, $S_{AE2}$, $RP_A$, $S_{AS}$, $S_{AB}$, $G_A$, $S_{DAS}$, $S_{DAB}$, $S_{BE1}$, $S_{BE2}$, $RP_B$, $S_{BS}$, $S_{BB}$, $G_X$, $S_{XB}$, $S_{XS}$.

4. The process of claim 3, wherein $W_1$ comprises essentially water and/or alcohol ROH.

5. The process of claim 4, wherein the transfer of energy from $W_1$ to the at least one component $Q_1$ or $Q_2$ occurs by $W_1$ being mixed at least partly with $Q_1$ or $Q_2$ after energy has been transferred from heating vapour $H_1$ or $H_4$ to $W_1$.

6. The process of claim 1, wherein R is selected from methyl or ethyl.

7. The process of claim 1, wherein $p_1 < p_3$.

8. The process of claim 1, wherein $Q_1$ and $Q_2$ are identical.

9. The process of claim 1, wherein the heating vapour $H_4$ is at least partially condensed so as to give a condensate $K_2$ by means of which a further step (f) in which the condensate $K_2$ is then used as condensate $K_1$ is carried out after step (h).

10. The process of claim 1, wherein the ratio of $p_1/p_4$ is in the range from 0.5 to 1.5.

11. The process of claim 1, wherein at least part of the vapour stream $S_{AB}$ taken off at the offtake point $E_{AK}$ at the upper end of the rectification column $RD_A$ is fed to the reaction column $RR_A$ at least as part of the feed stream $S_{AE1}$ and, in cases in which step (a2) is carried out in the process of the invention, is alternatively or additionally fed to the reaction column $RR_B$ at least as part of the feed stream $S_{BE1}$.

12. The process of claim 1, wherein step (d) is carried out.

13. The process of claim 12, wherein at least part of the vapour stream $S_{XB}$ taken off at the offtake point $E_{XK}$ at the upper end of the at least one rectification column $RD_X$ is fed to the reaction column $RR_A$ at least as part of the feed stream $S_{AE1}$ and, in cases in which step (a2) is carried out in the process of the invention, is alternatively or additionally fed to the reaction column $RR_B$ at least as part of the feed stream $S_{BE1}$.

14. The process of claim 1, wherein step (a2) is carried out.

15. The process of claim 1, which is carried out continuously.

16. The process of claim 5, wherein R is selected from methyl or ethyl.

17. The process of claim 6, wherein $p_1 < p_3$.

18. The process of claim 7, wherein $Q_1$ and $Q_2$ are identical.

19. The process of claim 8, wherein the heating vapour $H_4$ is at least partially condensed so as to give a condensate $K_2$ by means of which a further step (f) in which the condensate $K_2$ is then used as condensate $K_1$ is carried out after step (h).

20. The process of claim 9, wherein the ratio of $p_1/p_4$ is in the range from 0.5 to 1.5.

* * * * *